(12) United States Patent
Lawrence et al.

(10) Patent No.: US 11,344,612 B2
(45) Date of Patent: May 31, 2022

(54) **VIRULENT *AEROMONAS* VACCINES AND METHODS**

(71) Applicant: MISSISSIPPI STATE UNIVERSITY, Starkville, MS (US)

(72) Inventors: Mark L. Lawrence, Starkville, MS (US); Attila Karsi, Starkville, MS (US); Hossam Abdelhamed, Starkville, MS (US)

(73) Assignee: Mississippi State University, Starkville, MS (US)

( * ) Notice: Subject to any disclaimer, the term of this patent is extended or adjusted under 35 U.S.C. 154(b) by 0 days.

(21) Appl. No.: 16/467,166

(22) PCT Filed: Dec. 8, 2017

(86) PCT No.: PCT/US2017/065401
§ 371 (c)(1),
(2) Date: Jun. 6, 2019

(87) PCT Pub. No.: WO2018/107083
PCT Pub. Date: Jun. 14, 2018

(65) Prior Publication Data
US 2020/0030428 A1 Jan. 30, 2020

Related U.S. Application Data

(60) Provisional application No. 62/431,484, filed on Dec. 8, 2016.

(51) Int. Cl.
*A61K 39/02* (2006.01)
*A61K 39/00* (2006.01)

(52) U.S. Cl.
CPC ........ *A61K 39/0208* (2013.01); *A61K 39/025* (2013.01); *A61K 2039/522* (2013.01);
(Continued)

(58) Field of Classification Search
None
See application file for complete search history.

(56) References Cited

U.S. PATENT DOCUMENTS 9,375,467 B2 * 6/2016 Lawrence ............... A61P 37/04
2004/0058332 A1 3/2004 Bilodeau et al.

OTHER PUBLICATIONS

Li et al (Huazhong Nongye Daxue Xuebo. 2006. 25(6): 654-658, Abstract Only).*

(Continued)

*Primary Examiner* — Jennifer E Graser
(74) *Attorney, Agent, or Firm* — Butler Snow LLP

(57) ABSTRACT

*Aeromonas hydrophila* is a reemerging pathogen of channel catfish (*Ictalurus punctatus*); recent outbreaks from 2009 to 2014 have caused the loss of more than 12 million pounds of market size catfish in Alabama and Mississippi. Genome sequencing revealed a clonal group of *A. hydrophila* isolates with unique genetic and phenotypic features that is highly pathogenic in channel catfish. Comparison of the genome sequence of a representative catfish isolate (ML09-119) from this virulent clonal group with lower virulence *A. hydrophila* isolates revealed four fimbrial proteins unique to strain ML09-119. In this work, we expressed and purified four *A. hydrophila* fimbrial proteins (FimA, Fim, MrfG, and FimOM) and assessed their ability to protect and stimulate protective immunity in channel catfish fingerlings against *A. hydrophila* ML09-119 infection for vaccine development. Our results showed catfish immunized with FimA, Fim, FimMrfG, and FimOM exhibited 59.83%, 95.41%, 85.72%, and 75.01% relative percent survival, respectively, after challenge with *A. hydrophila* strain ML09-119. Bacterial concentrations in liver, spleen, and anterior kidney were significantly ($p<0.05$) lower in vaccinated fish compared to the non-vaccinated sham groups at 48 h post-infection. However, only the Fim immunized group showed a significantly higher antibody titer in comparison to the non-vaccinated treatment group ($p<0.05$) at 21 days post-vaccination. Altogether, Fim and FimMrfG recombinant proteins have potential for vaccine development against virulent *A. hydrophila* infection. Genomic subtraction revealed three outer membrane proteins present in strain ML09-119 but not in the low virulence reference *A. hydrophila* strain; the major outer membrane protein OmpAI (OmpA1), TonB-dependent receptor (TonB-DR), and transferrin-binding protein A (TbpA). Here, the genes encoding OmpAI, tonB-DR, and tbpA were cloned from *A. hydrophila* ML09-119 and were expressed into *Escherichia coli*. The purified recombinant OmpA, TonB-DR, and TbpA proteins had estimated molecular weights of 37.26, 78.55, and 41.67 kDa, respectively. Catfish fingerlings vaccinated with OmpA1, TonB-DR, and TbpA emulsified with non-mineral oil adjuvant were protected against the subsequent *A. hydrophila* ML09-119 infection with 98.59%, 95.59%, and 47.89% relative percent survival (RPS), respectively. Furthermore, the mean liver, spleen, and anterior kidney bacterial loads were significantly lower in catfish vaccinated with the OmpA1 and TonB-DR than the non-vaccinated control group. ELISA demonstrated that catfish immunized with OmpA1, TonB-DR, and TbpA produce significant antibody response by 21 days post-immunization. Therefore, data generated during the study suggest that OmpAI and TonB-DR proteins could be used as potential candidates for vaccine development against *A. hydrophila* epidemic strain infection. However, TbpA protein failed to provide such strong protection. Recombinant ATPase from *A. hydrophila* also showed promise as a vaccine antigen. A live attenuated vaccine was prepared that combined the advantages of a live attenuated vaccine (ESC-NDKL1 (ΔgcvPΔsdhCΔfrdA) mutant of *Edwardsiella ictaluri*) against enteric septicemia of catfish (ESC) and three immunogenic recombinant proteins (Fim, FimMrfg, and ATPase) against *A. hydrophila* infection. Our results showed channel catfish fingerlings immersion-vaccinated with ESC-NDKL1::pETfim, ESC-NDKL1::pETmrfG, and ESC-NDKL1::pETATPase exhibited 100%, (Continued)

91.67%, and 100% percent survival after challenge with the *A. hydrophila* ML09-119, which was significantly less than non-vaccinated group (88.89% mortality). In a second study, Catfish immunized with NDKL1::pETfim, ESC-NDKL1::pETmrfG, ESC-NDKL1::pETATPase had significantly ($p<0.05$) lower mortalities than sham-vaccinated group.

7 Claims, 10 Drawing Sheets

Specification includes a Sequence Listing.

(52) U.S. Cl.
 CPC .. *A61K 2039/523* (2013.01); *A61K 2039/552* (2013.01); *A61K 2039/55566* (2013.01); *A61K 2039/70* (2013.01)

(56) References Cited

OTHER PUBLICATIONS

Thanga Vijii et al (Dis Aquat Organ. Apr. 29, 2013;104(1):45-57).*
Abdelhamed et al., Protective efficacy of four recombinant fimbriai proteins of virulent Aeromonas hydrophila strain ML09-119 in channel catfish. Vet Microbiol. Dec. 25, 2016 (published in advance online Oct. 29, 2016), vol. 197, pp. 8-14. Especially abstract; p. 9, col. 1, para 3; p. 10, coi 1, para 2-3; p. 13, col. 1, para 1; p. 13, col. 1, para 3; p. 13, col. 2, para 2; p. 14, col. 1, para 2.
Zhang et al., Identification and Characterization of Putative Virulence Genes and Gene Clusters in Aeromonas hydrophila PPD134/91, Appl and Environ. Microbiology, Aug. 2005, p. 4469-4477.

* cited by examiner

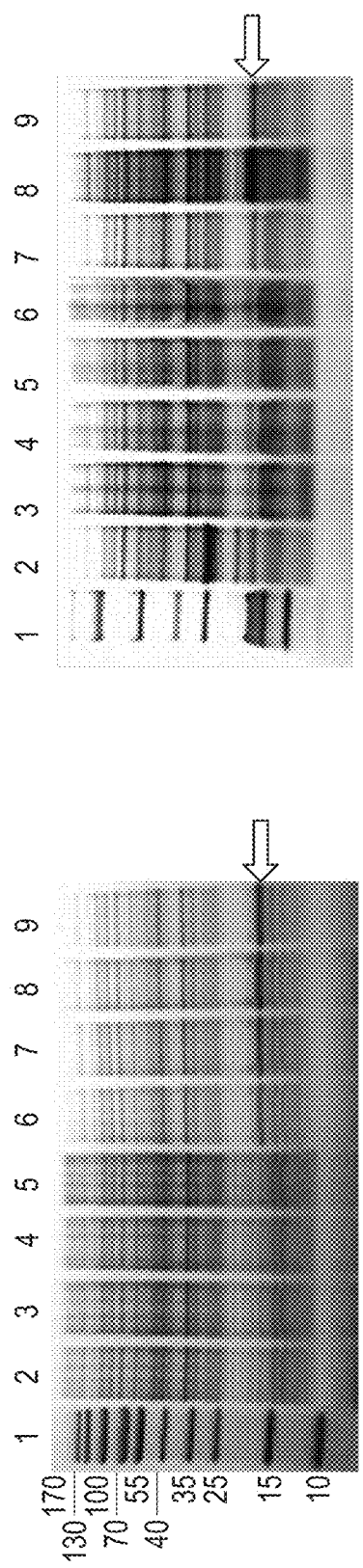
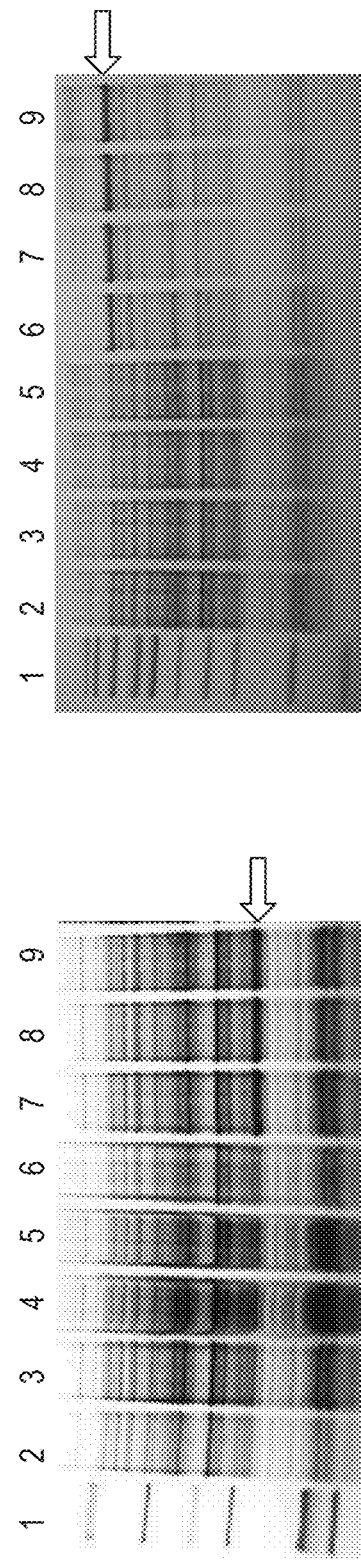
FIG. 1A
FIG. 1B
FIG. 1C
FIG. 1D

SEQUENCE LISTING

```
<160> NUMBER OF SEQ ID NOS: 17

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aaaagcttac tggtaggtca tgataaagtc g                                    31

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggatccta tgaaacccat gatgaaacc                                       29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aaggatcctt ggaaaatgag gtttgcagt                                       29

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaaagcttct gataattcat gacaaagtct gc                                   32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 5
aaaagcttat aggtcagctt gagggttgac                                              30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaggatccct gaaggaggta acgatgaacc                                              30

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagagctcaa cgggtctcag tgacagctc                                               29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagaattccc ccttacagac agtgacgat                                               29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggatccca agagggtgtt atgtcagagc                                              30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagtcgaccc tgatgtccaa gttcatgtat                                              30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 11
aaaagcttct tgatcccggt cagtcgta                                              28

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaggatccat gtcatccatg atatttggac a                                          31

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagtcgacat gtcataggcg ctccatctt                                             29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aaggatccgg cataaagcct gaattcctt                                             29

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaggatcctt gaaaaatgag aacgttgata ca                                         32

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaaagctttc tacctggaga agtgagccta                                            30

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 17

His His His His His His
1               5
```

VIRULENT *AEROMONAS* VACCINES AND METHODS

GOVERNMENT SUPPORT

This invention was made with government support under 2013-67015-21313 awarded by the National Institute of Food and Agriculture, USDA. The government has certain rights in the invention.

SEQUENCE LISTING

The instant application contains a Sequence Listing which has been filed electronically in ASCII format and is hereby incorporated by reference in its entirety. Said ASCII copy, created on Oct. 18, 2019, is named 028186_179578_SL.txt and is 4,129 bytes in size.

FIELD OF THE INVENTION

The present invention is generally directed toward vaccines and methods of making and using the same, and more specifically to vaccines utilizing recombinant fimbrial and outer membrane proteins against virulent strains of *Aeromonas hydrophila*.

BACKGROUND OF THE INVENTION

*Aeromonas hydrophila* is an important and reemerging Gram-negative bacterial pathogen associated with disease outbreaks in farmed fish with estimated losses of millions of dollars per annum (Fang et al., 2004) and more recently the cause of outbreaks from 2009 to 2014 that have caused the loss of more than 12 million pounds of market size catfish in Alabama and Mississippi. *A. hydrophila* is ubiquitous in aquatic environments and is responsible for causing a number of different diseases including "Motile *Aeromonas* Septicemia" (MAS), "Hemorrhagic Septicemia", "Ulcer Disease," and "Red-Sore Disease" (Esteve et al., 1995) in carp, tilapia, perch, salmon, catfish, and other fish species (Janda and Abbott, 2010).

*A. hydrophila* was not historically considered a pathogen of major concern in channel catfish aquaculture. However, since April of 2009, a clonal population of highly virulent *A. hydrophila* (VAh) strains have been isolated from disease outbreaks on commercial catfish farms in western Alabama (Hemstreet, 2010). Experimental infection indicated that epidemic VAh isolates are highly virulent for channel catfish (*Ictalurus punctatus*) compared with reference isolates of *A. hydrophila* (RAh) that are considered as opportunistic bacterial pathogen isolated from stressed fish (Pridgeon and Klesius, 2011). Moreover, there are considerable sequence differences between the VAh isolates and RAh strain that may account for their emergence as highly virulent strains in catfish ponds (Gresham, 2014; Hemstreet, 2010). Since then, disease outbreaks have spread to Mississippi and Arkansas (Pridgeon and Klesius, 2011). Until 2014, this outbreak has been responsible for an estimated loss of more than $12 million in commercially raised catfish operations in the Southeastern United States (Hossain et al., 2014). The signs of *A. hydrophila* infection caused by these VAh in catfish include acute onset of anorexia, hemorrhage in muscles and visceral organs, and bloody ascites. Outbreaks are associated primarily with marketable size catfish with mortality rates up to 50-60%.

MAS infection can be difficult to treat in aquaculture systems due to antibiotic resistance (Shariff, 1998). Therefore, vaccination would be a more efficient method to control and prevent *A. hydrophila* infection. During recent years, numerous studies investigated the use of several recombinant surface and extracellular proteins as vaccines against *A. hydrophila* infection, including Omp38 (Wang et al., 2013b), Aha1 and OmpW (Maiti et al., 2012), extracellular protease (Wu et al., 2012), Omp48 (Khushiramani et al., 2012), flagellar protein FlgK (Yeh and Klesius, 2012), and Omp-G (Guan et al., 2011). Although these different preparations have provided varying degrees of protection in fish, a commercial vaccine for protection of farmed fish against *A. hydrophila* infection does not exist.

The outer membrane proteins (OMPs) constitute approximately 50% of the outer membrane (OM) mass and genes encoding OMPs account for 2-3% of the entire genome (Koebnik et al., 2000; Wimley, 2003). The OMPs typically display β-barrel structural architecture and are involved in bacterial adaptive responses such as solute and ion uptake, iron acquisition, antimicrobial resistance, serum resistance, and bile salt resistance (Lin et al., 2002). The functional roles of many OMPs are associated with the virulence of several Gram-negative bacterial species, and some play roles in facilitating adherence, colonization, and persistence in the host (Ebanks et al., 2005; Vazquez-Juarez et al., 2004).

The outer membrane protein A (OmpA) is one of the major integral proteins of OM and plays structural and physiological roles, which includes maintaining the integrity of the bacterial cell surface, serving as receptors for phage and colicin, participating in biofilm formation, mediating F-dependent conjugation of *Escherichia coli* K1, and contributing to serum resistance (Koebnik et al., 2000; Mittal et al., 2011; Schweizer and Henning, 1977). In addition, OmpA is immunogenic and can illicit antibodies with opsonic, bactericidal, or protective activities (Mahasreshti et al., 1997). Recently, OmpA has been shown to exist as two different allelic forms, OmpA1 and OmpA2. These two alleles have specific differences in the amino acid sequence (Power et al., 2006).

Consistent with their roles in iron acquisition, TonB-dependent receptor (also "TonB-DR") serves to detect signals from outside the bacterial cell and transmits them across two membranes into the cytoplasm, leading to transcriptional activation of target genes. TonB interacts with ligand-bound outer membrane receptors and functions to transduce energy derived from the proton motive force (PMF) to allow active transport of iron siderophores and vitamin B12 through transporters located in the outer membrane (Letain and Postle, 1997). TonB-dependent receptors have been found to be essential for virulence in pathogenic bacteria (Alvarez et al., 2008; Tauseef et al., 2011).

In Gram-negative bacteria, the components of the transferrin receptor consist of two iron-regulated OMPs termed transferrin-binding protein A (TbpA) and transferrin-binding protein B (TbpB) (Cornelissen and Sparling, 1994). Tbps have been identified as potential vaccine candidates since their discovery (Schryvers and Morris, 1988). TbpA is an integral membrane protein and is a member of the family of TonB-dependent outer membrane proteins that include siderophore receptors. TbpA is required to bind transferrin and serves as a channel for transport of iron across the OM (Kenney and Cornelissen, 2002). The proposed role for iron transport is supported by the lack of expression of TbpA results in mutants incapable of growth on medium containing transferrin as the sole iron source. TbpA has been identified in pathogenic bacteria such as *Neisseria meningitidis* (Irwin et al., 1993), *Neisseria gonorrhoeae* (Cornelissen et al., 1992), *Moraxella catarrhalis* (Luke and Campagnari, 1999), and *Haemophilus influenzae* (Gray-Owen et al., 1995).

BRIEF DESCRIPTION OF THE DRAWINGS

Further advantages of the invention will become apparent by reference to the detailed description of preferred embodiments when considered in conjunction with the drawings:

FIGS. 1A-1D depict four SDS-PAGE gels with Coomassie blue stain showing expression of recombinant *A. hydrophila* ML09-119 proteins FimA (FIG. 1A), Fim (FIG. 1B), FimMrfG (FIG. 1C), and FimOM (FIG. 1D) in *E. coli* BL21 (DE3) after induction with 100 mM IPTG. In all panels—Lanes: (1) standard protein marker, (2) uninduced 2 h, (3) uninduced 4 h, (4) uninduced 6 h, (5) uninduced 8 h, (6) induced 2 h, (7) induced 4 h, (8) induced 6 h, and (9) induced 8 h. Arrows indicate recombinant proteins in each panel.

DETAILED DESCRIPTION

Figure 2:
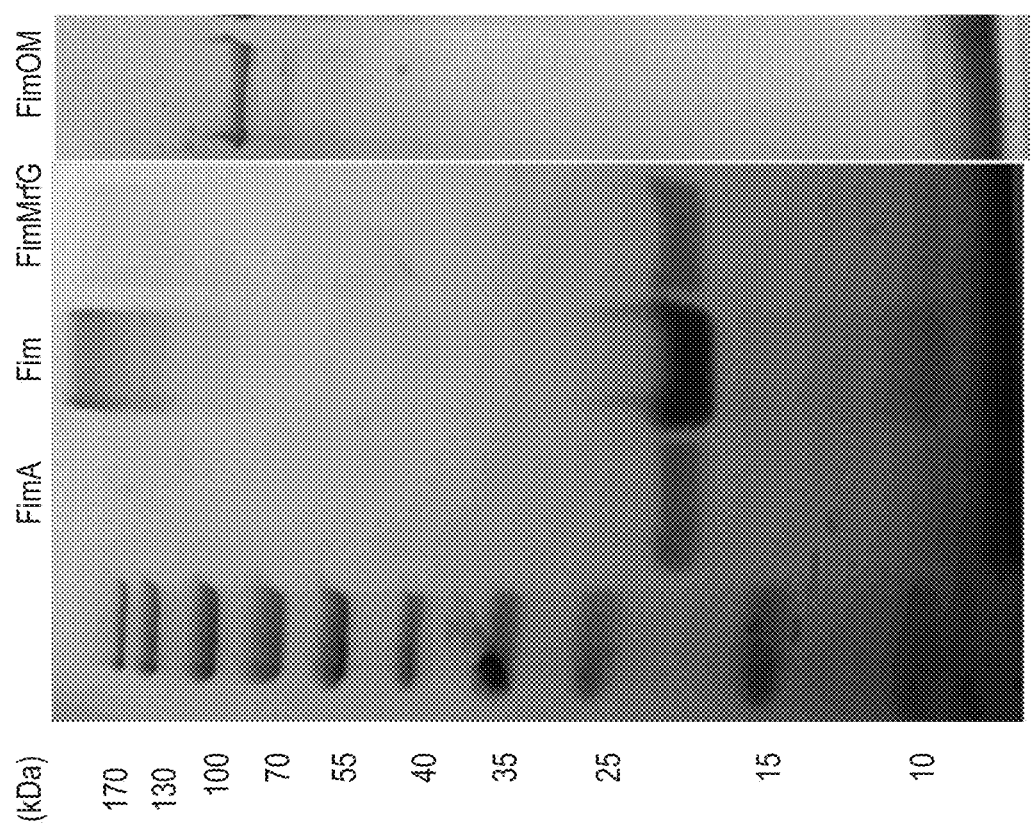
FIG. 2 depicts an SDS-PAGE gel with Coomassie blue stain showing purified recombinant FimA, Fim, FimMrfG, and FimOM. Molecular weights in kilodaltons (kDa) are shown for the standard protein marker in the right column.

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

*A. hydrophila* strain ML09-119 was isolated from an outbreak of MAS in a commercial catfish operation in western Alabama (Tekedar et al., 2013), and it is our representative strain of the clonal group of VAh strains. Using comparative genomics, we determined that some fimbrial proteins are unique to VAh strains compared to historical *A. hydrophila* strains isolated from catfish aquaculture. One goal was to amplify, express, and purify four of these VAh-unique fimbrial proteins from *A. hydrophila* strain ML09-119 [(P pilus assembly protein, pilin FimA (AGM42215.1), fimbrial protein (AGM42222.1), fimbrial protein MrfG (AGM42218.1), and fimbrial biogenesis outer membrane usher protein (AGM42220.1)]. Further, we determined whether these proteins have potential to protect and stimulate antibody response in catfish against *A. hydrophila* ML09-119 infection.

Genomic subtraction based on differences between VAh (ML09-119 strain) with nonpathogenic RAh isolates also revealed three outer membrane proteins (OMPs) present in virulent strain ML09-119 but not in the low virulence RAh; the major outer membrane protein OmpAI (OmpA1: AHML_06755), TonB-dependent receptor (TonB-DR: AHML_05675), and transferrin-binding protein A (TbpA: AHML_13490). Therefore, a second goal was to express and purify recombinant OmpA1, TonB-DR, and TbpA proteins from *A. hydrophila* strain ML09-119. We also assessed the level of protection and antibody responses afforded by these three proteins against infection with *A. hydrophila* strain ML09-119 in catfish.

Material and Methods

Bacterial Strains and Plasmids

Bacterial strains and plasmids are listed in Table 1. *A. hydrophila* strain ML09-119 (Griffin et al., 2013) was isolated in 2009 from a large-scale disease outbreak in a commercial catfish farm in Alabama. It is a representative strain of the clonal group of virulent *A. hydrophila* that have impacted U.S. channel catfish aquaculture. The strain was grown on brain heart infusion (BHI) agar or broth (Difco, Sparks, Md., USA) and incubated at 37° C. *Escherichia coli* strains NovaBlue (Novagen, Madison, Wis., USA) and Rosetta II/BL21 (DE3) (EMD Millipore; Invitrogen, Carlsbad, Calif., USA, respectively) were used for cloning and expression, respectively. *E. coli* strains were cultured on Luria-Bertani (LB) agar or broth (Difco) supplemented with appropriate selection and incubated at 37° C. throughout the study. The expression vector pET-28a (Novagen) was used for expression of recombinant proteins. Whenever required, isopropyl-β-D-thiogalactopyranoside (IPTG), kanamycin (Kan, 50 µg/ml), ampicillin (Ap, 100 µg/ml), and/or colistin (Col, 2.5 µg/ml) (Sigma-Aldrich, Saint Louis, Minn., USA) were added to culture medium.

TABLE 1

Bacterial strains and plasmids used

| Strain or plasmid | Description | Source |
|---|---|---|
| *A. hydrophila* ML09-119 | Isolate from a disease outbreak on a commercial catfish farm | (Griffin et al., 2013) |
| *E. coli* | | |
| NovaBlue | endA1 hsdR17(rK12− mK12+) supE44 thi-1recA1 gyrA96 relA1 lac F′[proA+B+ lacIqZΔM15 ::Tn10(TcR)] | Novagen |
| BL21(DE3) | F⁻ ompT hsdS gal; expression host, vaccine delivery vector | Invitrogen |
| Rosetta II (DE3) | F⁻ ompT hsdSB($r_B$ - $m_B$ -) gal dcm (DE3) pRARE2 (Cam$^R$) | EMD Millipore |
| Plasmid | | |
| pET-28a | Expression vector; Km$^r$ | Novagen |
| pETfimA | pET-28a,:: fimA | This study |
| pETfim | pET-28a,:: fim | This study |
| pETmrfG | pET-28a,:: fimMrfG | This study |
| pETom | pET-28a,:: fimOm | This study |
| pETAhompA | pET-28a,:: ompAI | This study |
| pETAhtonB | pET-28a,:: tonB-DR | This study |
| pETAhtbpA | pET-28a,:: tbpA | This study |
| pETatpase | pET-28a,:: atpase | This study |

Construction of Four Fimbrial Protein Expression Plasmids

The coding regions of selected fimbrial genes were amplified by PCR using primers synthesized by Sigma-Aldrich. Two different restriction sites were incorporated into primer ends for cloning. The primers and restriction sites used are listed in Table 2. Product sizes were 588 bp, 438 bp, 570 bp, and 2566 bp for fimA, fim, fimMrfG, and fimOm, respectively. The amplified coding regions were purified using a QIAquick Gel Extraction Kit (Qiagen, Valencia, Calif., USA), digested, and ligated into the corresponding sites in linearized pET-28a. Ligation product was transformed into NovaBlue competent cells by heat shock at 42° C. Positive clones were selected on LB Kan plates and verified by colony PCR using T3 and T7 terminator primers to confirm the in-frame insertion. Four recombinant plasmids (pETfimA, pETfim, pETmrfG, and pETom) were isolated from *E. coli* NovaBlue, then transformed into competent BL21 (DE3).

TABLE 2

Properties of *A. hydrophila* ML09-119 fimbrial proteins and oligonucleotide primers used for PCR amplification

| Protein | Locus tag | Number of nucleotides/ amino acids | M.W. (kDa) | Iso-electric point | Primer | Sequence | Restriction enzyme |
|---|---|---|---|---|---|---|---|
| P pilus assembly protein, pilin FimA | AHML_02150 | 591/197 | 20.59 | 4.45 | FIM1-F | AAAAGCTT ACTGGTAG GTCATGAT AAAGTCG (SEQ ID NO: 01) | HindIII |
| | | | | | FIM1-R | AAGGATCC TATGAAAC CCATGATG AAACC (SEQ ID NO: 02) | BamHI |

TABLE 2-continued

Properties of A. hydrophila ML09-119 fimbrial proteins and oligonucleotide primers used for PCR amplification

| Protein | Locus tag | Number of nucleotides/ amino acids | M.W. (kDa) | Iso-electric point | Primer | Sequence | Restriction enzyme |
|---|---|---|---|---|---|---|---|
| Fimbrial protein | AHML_02185 | 441/147 | 20.11 | 4.982 | FIM2-F | AAGGATCCTTGGAAAATGAGGTTTGCAGT (SEQ ID NO: 03) | BamHI |
|  |  |  |  |  | FIM2-R | AAAAGCTTCTGATAATTCATGACAAAGTCTGC (SEQ ID NO: 4) | HindIII |
| Fimbrial protein MrfG | AHML_02165 | 561/186 | 19.56 | 9.362 | MrfG-F | AAAAGCTTATAGGTCAGCTTGAGGGTTGAC (SEQ ID NO: 5) | HindIII |
|  |  |  |  |  | MrfG-R | AAGGATCCCTGAAGGAGGTAACGATGAACC (SEQ ID NO: 6) | BamHI |
| Fimbrial biogenesis outer membrane usher protein | AHML_02175 | 2538/846 | 93.52 | 4.999 | OM-F | AAGAGCTCAACGGGTCTCAGTGACAGCTC (SEQ ID NO: 07) | SacI |
|  |  |  |  |  | OM-R | AAGAATTCCCCCTTACAGACAGTGACGAT (SEQ ID NO: 08) | EcoRI |
| ATPase | AHML_21010 | 2160/720 | 81.51 | 5.123 | ATPase-F | ~~AAGTCGAC~~ AAGGATCCCAAGAGGGT[[H]]GTTATGTCA[[F]]GAGC (SEQ ID NO: 09) | SalI |
|  |  |  |  |  | ATPase-R | AAGTCGACCCTGATGTCCAAGTTCATGTAT (SEQ ID NO: 10) | SalI |

<sup>a</sup>Bold letters at the 5' end of the primer sequence represent RE site added. AA nucleotides were added to the end of each primer containing a RE site to increase the efficiency of enzyme cut.

Expression of Four Recombinant Fimbrial Proteins in BL21 (DE3)

E. coli BL21 (DE3) carrying recombinant plasmids was grown in LB broth containing Kan with constant shaking at 37° C. until cultures reached an optical density (600 nm) of 0.5-0.6; subsequently, bacteria were induced with 100 mM IPTG for 8 h at 37° C. Whole bacterial proteins were isolated using BUGBUSTER protein extraction reagent (Novagen) and solubilized in tricine sample buffer (Bio-Rad Laboratories, Hercules, Calif., USA) for 5 min at 80° C. Protein separation was conducted using 12% SDS-PAGE (Laemmli, 1970) to check expression of each fimbrial protein. Non-recombinant E. coli BL21 (DE3) and uninduced recombinant clone were used as controls. After positive clones were identified, bacteria were stored at −80° C. in 20% glycerol.

Purification of Recombinant Fimbrial Proteins

Fimbrial proteins were purified by His-Bind (Novagen) resin column. Briefly, E. coli BL21 (DE3) was grown in 500 ml of LB broth and induced by IPTG. Bacteria were harvested by centrifugation (12,000×g for 20 min at 4° C.), and pellets were lysed using BUGBUSTER protein extraction reagent with BENZONASE nuclease and protease inhibitor cocktail set III (Sigma). Soluble fractions were removed by centrifugation, and recombinant proteins were purified from inclusion body pellets by suspending in lysis buffer (Tris-HCl buffer pH 8.0, 6 M urea) with gentle sonication (4 cycles, 10 s each) on ice. After centrifugation (12,000×g for 20 min at 4° C.), recombinant protein was bound to resin column, washed (0.5 M NaCl, 60 mM imidazole, 20 mM Tris-HCl, pH 7.9), and eluted in 1 M imidazole, 0.5 M NaCl, 20 mM Tris-HCl, pH 7.9. Protein yield was determined on a spectrophotometer at 280 nm, and purity was assessed by SD S-PAGE. The identity of the recombinant proteins was confirmed by MALDI-TOF mass spectrometry.

Construction of the OMP Recombinant Plasmids and Proteins Expression

The DNA fragments carrying ompAI (AHML_06755), tong DR (AHML_05675), and tbpA (AHML_13490) genes were amplified from A. hydrophila strain ML09-119 by PCR using the primer pairs shown in Table 3). The three amplified products were purified with the QIAquick PCR purification kit (Qiagen, Valencia, Calif., USA), cut with pairs of restriction endonucleases whose recognition sequences were incorporated into the primers (shown in bold letters in Table 3), and gel purified. Each processed DNA fragment was ligated to pET-28a cut with the same restriction endonucleases. Aliquots of ligated vector and insert were transformed to chemically competent NovaBlue cells, and were selected on LB agar plates supplemented with Kan. Plasmid DNA was extracted from positive clones, cut with appropriate restriction endonucleases, and run in 1% agarose gel. Candidates with the appropriate migration patterns were sequenced using T3 and T7 terminator primers to confirm the correct orientation of the insert. The three recombinant plasmids (pETAhompAI, pETAhtonB, and pETAhtbpA) were introduced into Rosetta II (DE3) by transformation.

The expression of OmpA, TonB-DR, and TbpA proteins were checked in small scale (25 ml) culture. Well-isolated colonies of Rosetta II (DE3) carrying the recombinant plasmids were grown on LB broth supplemented with Kan (50 µg/ml). Cultures were induced at an optical density at 600 nm (OD600) of 0.6 to 0.8 by adding 100 mM IPTG, and incubation was continued for 6 h. Whole cell protein samples at different time points were prepared and analyzed by running 12% SDS-PAGE. Non-recombinant cells and uninduced recombinant clone were used as negative controls.

Purification of OmpA1, TonB-DR, and TbpA Proteins Expressed by E. coli

The three proteins OmpA1, TonB-DR, and TbpA containing six histidine tags (His6) (SEQ ID NO: 17) were purified by HIS-BIND (Novagen) resin column according to the manufacturer's protocols. The recombinant OmpA1 protein was extracted following a method described previously (Yadav et al., 2014) with minor modifications. Briefly, recombinant clones were grown in 500 ml of LB broth and induced by IPTG for 6 h. The cells were then harvested by centrifugation (14,000 rpm for 20 min at 4° C.), and the pellet lysed using lysis buffer (50 mM Tris-HCl, pH 8.0, 10 mM EDTA, 10 mg/ml lysozyme) followed by sonication (4 cycles, 10 s) on ice. The sonicated solution was centrifuged, and then pellet was washed with pengu buffer (0.2 M sodium phosphate buffer pH 7.3, 1 mM EDTA, 50 mM NaCl, 5% glycerol, and 1 M urea), followed by wash with homogenization buffer (50 mM Tris-HCl, pH 8.0, 100 mM NaCl, 0.5% TritonX-100, 0.1% sodium-azide). The pellet was solubilized in solubilization buffer (6 M guanidinium chloride, 10 mM Tris-HCl, pH 8.0, 500 mM NaCl) for 1 h at 4° C. followed by centrifugation (13,000 rpm for 20 min at 4° C.). The clarified supernatant was loaded onto a HIS-BIND column prepacked with Ni2+-charged resin that had been preequilibrated with 10 ml of binding buffer. The non-specific proteins were removed by applying binding buffer followed by wash buffer (6 M urea, 500 mM NaCl, 20 mM imidazole, and 20 mM Tris-HCl [pH 7.9]). The recombinant OmpA1 protein was then eluted with an elution buffer (6 M urea, 1 M imidazole, 250 mM NaCl, 10 mM Tris-HCl) into small fractions. The identity and purity of OmpA1 protein was determined by 12% SDS-PAGE. Protein yield was determined on a spectrophotometer at 280 nm.

For purification of TonB-DR recombinant protein, expression was induced as described earlier by addition of IPTG at OD600=0.6. The cell pellet were collected by centrifugation and suspended in 100 mM sodium phosphate a pH 7.9 and gently sonicated. The cleared supernatant was loaded to

TABLE 3

Properties of A. hydrophila ML09-119 OmpA1, TonB-DR, and TbpA proteins and oligonucleotide primers used for PCR amplification

| Proteins | Locus tag | M.W. (kDa) | Primers | Sequence | RE |
|---|---|---|---|---|---|
| OmpAI | AHML_06755 | 37.26 | OmpAF | AAAAGCTTCTTGATCCCGGTCAGTC GTA (SEQ ID NO: 11) | HindIII |
|  |  |  | OmpAR | AAGGATCCATGTCATCCATGATATT TGGACA (SEQ ID NO: 12) | BamHI |
| TonB-DR | AHML_05675 | 78.55 | TonBF | AAGTCGACATGTCATAGGCGCTCC ATCTT (SEQ ID NO: 13) | SalI |
|  |  |  | TonBR | AAGGATCCGGCATAAAGCCTGAAT TCCTT (SEQ ID NO: 14) | BamHI |
| TbpA | AHML_13490 | 41.67 | TbpAF | AAGGATCCTTGAAAAATGAGAACG TTGATACA (SEQ ID NO: 15) | BamHI |
|  |  |  | TbpAF | AAAAGCTTTCTACCTGGAGAAGTG AGCCTA (SEQ ID NO: 16) | HindIII |

[a]Bold letters at the 5' end of the primer sequence represent RE site added. AA nucleotides were added to the end of each primer containing a RE site to increase the efficiency of enzyme cut.

equilibrated resin. The TonB-DR recombinant protein was eluted from resin column with the elution buffer and subjected to SDS-PAGE in order to confirm purity.

To purify TbpA protein, 500 ml of induced bacteria culture was harvested by centrifugation and the pellets lysed using BUGBUSTER protein extraction reagent (Novagen) with gentle sonication followed by centrifugation. The soluble fraction was mixed with binding buffer and bound to a packed resin column. After elution using elution buffer, the eluted fractions of TbpA recombinant protein was subjected to SDS-PAGE.

Establishment of an Immersion Challenge Model for *A. hydrophila* ML09-119 in Catfish To determine the exposure time and temperature that causes 50% mortalities (LD50) in channel catfish by bath immersion with *A. hydrophila* ML09-119, fish were divided into four groups of four replicates with 40 fish in each group (10 fish/tank). Immersion challenge dose was $1.7 \times 10^{10}$ colony forming unit (CFU)/ml in water. The first group was challenged by immersion for 3 h at 25° C., the second group by immersion for 6 h at 25° C., the third group by immersion for 3 h at 30° C., and the last group by immersion for 6 h at 30° C. Fish were monitored daily for two weeks, and the cause of mortality was confirmed by isolating bacteria from liver, spleen, and anterior kidney. Control fish in each group were given an equal volume of BHI broth. The experiment was performed twice.

Vaccine Efficacy of Recombinant Fimbrial Proteins

The vaccine efficacy trial was performed at Mississippi State University according to a protocol approved by the Institutional Animal Care and Use Committee (IACUC). On the day of immunization, the four fimbrial proteins FimA, Fim, FimMrfG, and FimOM were mixed with the non-mineral oil adjuvant Montanide ISA 763 AVG (Seppic, Paris, France) at a ratio of 30:70 fimbrial protein to adjuvant with final concentration of 250 µg/ml of each recombinant protein. Specific pathogen free channel catfish (mean weight: 68.77 g) were stocked in 40-L tanks supplied with flow-through dechlorinated municipal water with constant aeration and fed twice daily. Water temperature was maintained at 30° C. throughout the experiments. Fish were divided into seven treatments with five replicate tanks and 20 fish/tank: non-vaccinated control; PBS-adjuvant injected treatment; heat killed *A. hydrophila*-injected treatment (0.1 ml of $1 \times 10^6$ killed bacteria/ml); and four treatments injected intraperitoneally with 0.1 mL of recombinant fimbrial protein. Fish were anesthetized using tricaine methane sulfonate (MS-222) for injections.

Three weeks post-vaccination, fish were experimentally infected by immersion with *A. hydrophila* ML09-119 (approximately $2.3 \times 10^{10}$ CFU/ml) for 6 h at 30° C. At 48 h post-infection, a total of five fish (one fish per tank) from each treatment were euthanized, and liver, spleen, and anterior kidney tissues were collected aseptically. Tissues were homogenized in 1 ml PBS each. Tissue suspensions were diluted serially and spread in triplicate on BHI agar plates containing Amp and Col. Plates were incubated at 37° C. for 48 h, and viable bacterial colonies were enumerated.

The remaining fish were monitored for mortalities daily for two weeks, and relative percent survival (RPS) was calculated based on the formula RPS=[1−(% mortality in vaccinated group/% mortality in control group)]×100 (Amend, 1981).

Serum Antibody Response in Recombinant Fimbrial Protein Vaccinated Catfish

Three weeks post-vaccination and prior to experimental infection with strain ML09-119, ten fish per group (two fish per tank) were removed for blood collection. Blood was collected from the caudal vein, and after blood clotted overnight at 4° C., serum was obtained by centrifugation at 3500×g for 10 min.

Antibody titers were determined from the immunized fish serum by enzyme-linked immunosorbent assay (ELISA) (Waterstrat et al., 1991). Immulon™ plates (Bloomington, Minn., U.S.A.) were coated overnight at 4° C. with 50 µl per well of heat killed whole bacteria ($10^8$ CFU/ml). Wells were washed and blocked with 100 µl/well of 5% nonfat dry milk (Bio-Rad) in PBS overnight at 4° C. Wells were washed three times in PBS containing 0.05% Tween-20 (PBS-T). Fifty microliters of fish serum diluted 1:100 was added to each well. Plates were incubated for 1 h at 37° C. and washed. Fifty microliters of a 1:4 dilution of monoclonal antibody 9E1 (anti-catfish Ig) (Lobb and Clem, 1982; Miller et al., 1987) were added to each well, plates were incubated for 1 h at 37° C., and then they were washed.

Goat anti-mouse antibody conjugate (Fisher Scientific) was added, plates were incubated at room temperature for 1 h, and washed. Finally, 100 µl of p-nitrophenyl phosphate substrate (Sigma 104 phosphatase substrate) dissolved in 10% diethanolamine buffer was added to each well, and plates were incubated for 45 min at room temperature. Optical density of each well was measured at 405 nm in an ELISA Microplate Reader (CA, USA). Controls included wells with PBS buffer (in place of serum) and wells with known positive *A. hydrophila* immune sera. To standardize, average background absorbance for each plate was subtracted from the measured absorbance.

Statistical Analysis of Recombinant Fimbrial Protein Tests

The effect of vaccination with the different fimbrial proteins on fish survival after challenging with *A. hydrophila* was assessed with mixed model logistic regression using PROC GLIMMIX in SAS for Windows 9.4 (SAS Institute, Inc., Cary, N.C., USA). The number of live fish in a tank at the end of the trial was the outcome assessed using an events/trials syntax. Protein was the fixed effect assessed in the model. Tank within protein group was included as a random effect in the model. The wild type was the referent for comparisons of the effect of protein.

The effect of the different fimbrial proteins on the number of CFU in tissue samples and on ELISA titers was assessed by analysis of variance using PROC GLM in SAS for Windows 9.4. Separate models were used to assess CFU/g in liver, spleen, and anterior kidney samples as well as the ELISA results. The CFU/g data was transformed by first adding 1 to each CFU/g value and then taking the base 10 logarithm. The ELISA data was transformed by simply taking the base 10 logarithm of each ELISA value. The distribution of the residuals was evaluated for each model to determine the appropriateness of the statistical model for the data. If the effect of protein was found to be statistically significant, the least squares means were compared using the Dunnett adjustment for multiple comparisons with wild type as the referent. A significance level of 0.05 was used for all analyses.

Fish Vaccination and Evaluation of Protection with Recombinant OMPs

A total of 500 specific pathogen free (SPF) channel catfish fingerlings (12.91±0.82 g, 11.89±0.30 cm) were stocked in twenty 40-L tanks (25 fish per tank) with a continuous water flow system and aerated with compressed air diffused through air stones. Tanks were randomly assigned to OmpAI, TonB-DR, TbpA, PBS-adjuvant, and sham-vaccinated group (negative control) with four tanks per group. The fish were fed twice daily and acclimatized for one week.

On the day of immunization, the fish were anesthetized by immersion in tricaine methane sulfonate (MS-222) and intraperitoneally (IP) injected with 0.1 mL of recombinant proteins mixed with the non-mineral oil adjuvant Montanide ISA 763 AVG (Seppic, Paris, France) at a ratio of 30:70 protein to adjuvant with final concentration of 250 µg/ml of each recombinant protein. The negative control group was IP injected with PBS.

Three weeks post-vaccination, an immersion challenge with *A. hydrophila* ML09-119 was conducted for 6 h at 32° C. with approximately $4.3 \times 10^{12}$ CFU/ml. Mortalities were recorded for 2 weeks and the relative percent survival (RPS) was calculated. At 48 h post-infection, five fish were randomly selected from each treatment and euthanatized using MS-222. Liver, spleen, and anterior kidney were aseptically removed from each fish and weighed. Tissues were homogenized and the resulting suspension was serially diluted. The cell suspensions were spread on BHI agar plates which were incubated at 37° C. for 48 h and then viable bacterial colonies enumerated. The number of CFU/g of tissue was calculated for each fish.

Analysis of Antibody Response after Recombinant OMPs Vaccination

Before *A. hydrophila* ML09-119 challenge, a randomly selected eight fish per group (two fish per tank) was used to identify the antibody response. The blood samples were collected from fish and was allowed to coagulate overnight at 4° C. Serum was obtained by centrifugation at 8000 rpm for 10 min.

Fish serum was assayed for antibody response by enzyme-linked immunosorbent assay (ELISA). *Aeromonas hydrophila* was inactivated with heat for 3 h, washed and re-suspended in sterile PBS. Inactive bacterial suspension at a concentration of $10^8$ CFU/ml was used to coat a 96-well ELISA plate (Bloomington, Minn., U.S.A). Fifty microliters of fish serum diluted 1:100 collected from recombinant protein-vaccinated fish or from a control group were added to each well. Fifty microliters of a 1:4 dilution of monoclonal antibody 9E1 (anti-catfish Ig) (Lobb and Clem, 1982) were used as primary antibodies. Goat anti-mouse antibody conjugate (Fisher Scientific) was used as the secondary antibody, and p-nitrophenyl phosphate substrate (Sigma 104 phosphatase substrate) dissolved in 10% diethanolamine buffer was used as the substrate, according to manufacturer's recommendations. Plates were read at 405 nm in an ELISA Microplate Reader (CA, USA) to determine the optical density. Controls included wells in which PBS buffer was used in place of serum. To standardize, average background absorbance for each plate was subtracted from the measured absorbance.

Statistical Analysis of Recombinant OMPs Tests

The effect of the different recombinant OMPs test treatments on the mortality of fish challenged with *A. hydrophila* was assessed with mixed model logistic regression using PROC GLIMMIX in SAS for Windows 9.4 (SAS Institute, Inc., Cary, N.C., USA). The number of fish that had died in a tank by the end of the trial was the outcome assessed using an events/trials syntax. Treatment was the fixed effect assessed in the model with tank within treatment group included as a random effect. The results of the logistic regression models were reported as odds ratios with the BHI group and the Adjuvant group each used as referent for separate comparisons of the effect of treatment on mortality. The effect of the different treatments on the number of CFU in tissue samples was assessed by analysis of variance using PROC GLM in SAS for Windows 9.4. Separate models were used to assess CFU in liver, spleen, and anterior kidney samples. The CFU data was transformed by first adding 1 to each CFU value and then taking the base 10 logarithm. Treatment was the fixed effect in each of the models. The effect of the different treatments on the ELISA values was assessed by mixed model analysis using PROC MIXED in SAS for Windows 9.4. The ELISA data was transformed by taking the base 10 logarithm of each ELISA value. Treatment was the fixed effect with block used as a random effect in the model. If the effect of treatment was found to be statistically significant in the analysis CFU or ELISA values, the least squares means were compared using the Dunnett adjustment for multiple comparisons with either BHI or Adjuvant as the referent. The distribution of the residuals was evaluated for each model to determine the appropriateness of the statistical model for the data. A significance level of 0.05 was used for all analyses.

Results of Recombinant Fimbrial Protein Tests

Production of Four Recombinant Fimbrial Proteins of *A. hydrophila* ML09-119

Recombinant fimbrial proteins migrated to the expected size on Coomassie blue stained SDS-PAGE gels. No expression was observed with non-recombinant *E. coli* and uninduced recombinant clones, and optimal induction time with IPTG was determined to be 6-8 h (FIG. 1). The four fimbrial recombinant proteins (20.59 kDa, 20.11 kDa, 19.56 kDa, and 93.52 kDa for FimA, Fim, FimMrfG, and FimOM, respectively) were found in the insoluble fraction (FIG. 2). To further confirm these proteins, MALDI-TOF mass spectrometry amino acid sequencing was conducted, resulting in 100% identity with the published sequences (accession numbers AGM42215.1, AGM42222.1, AGM42218.1 and AGM42220.1) (data not shown).

Establishment of an Immersion Challenge Model of *A. hydrophila* ML09-119 in Catfish No mortalities occurred in the two treatments where fish were experimentally infected at 25° C. In addition, no mortalities occurred when fish were experimentally infected at 30° C. for 3 h. However, when fish were immersed for 6 h at 30° C., mortalities were 46.53% in the first trial and 52.33% in the second trial. In each trial, all fish mortalities occurred within 48 h of experimental infection. Therefore, this method was used as the *A. hydrophila* immersion challenge protocol for the recombinant fimbrial protein vaccine study.

Vaccine Efficacy of Recombinant Fimbrial Proteins

Figure 3:
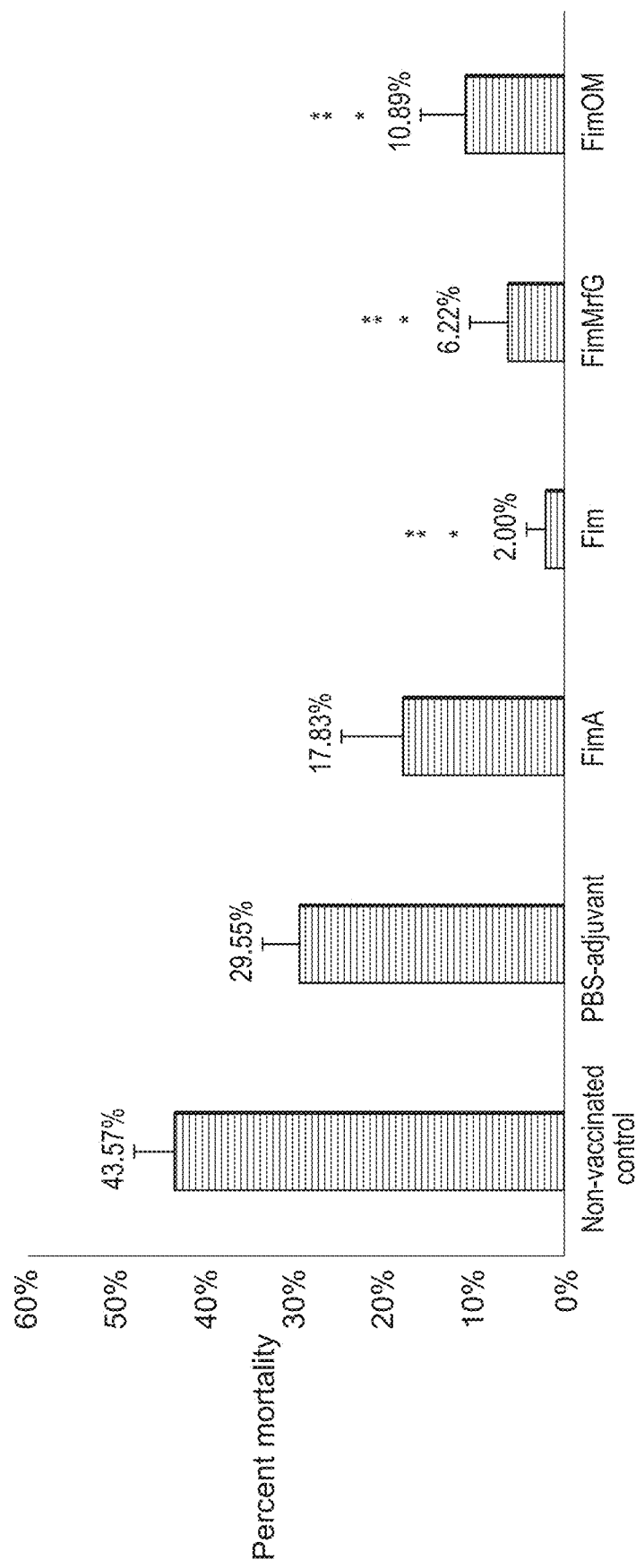
FIG. 3 is a bar graph showing percent mortalities in catfish vaccinated with FimA, Fim, FimMrfG, and FimOM recombinant proteins following experimental infection with *A. hydrophila* ML09-119 at three weeks post-vaccination. Data are the mean±SE of five replicate tanks (each containing 20 fish). Significant differences between vaccinated and non-vaccinated treatments are indicated with asterisks (*) ($p<0.05$). Significant differences between vaccinated treatments and PBS-adjuvant treatment are indicated with two asterisks (‡)($p<0.05$).

Significantly higher mortalities occurred in the non-vaccinated control treatment (43.57%) compared to mortalities in fish vaccinated with Fim (2.00%; p=0.0069), FimMrfG (6.22%; p=0.0058), and FimOM usher protein (10.89%; p=0.0171). There was no significant difference in mortalities between non-vaccinated control treatment and fish vaccinated with FimA (17.83%; p=0.0621), as well as fish injected with PBS-adjuvant (29.54%; p=0.3588) (FIG. 3). RPS for the four recombinant fimbrial proteins (FimA, Fim, FimMrfG, and FimOM) was 59.83%, 95.41%, 85.72%, and 75.01%, respectively. RPS for the PBS-adjuvant treatment was 32.19%.

Figure 4:
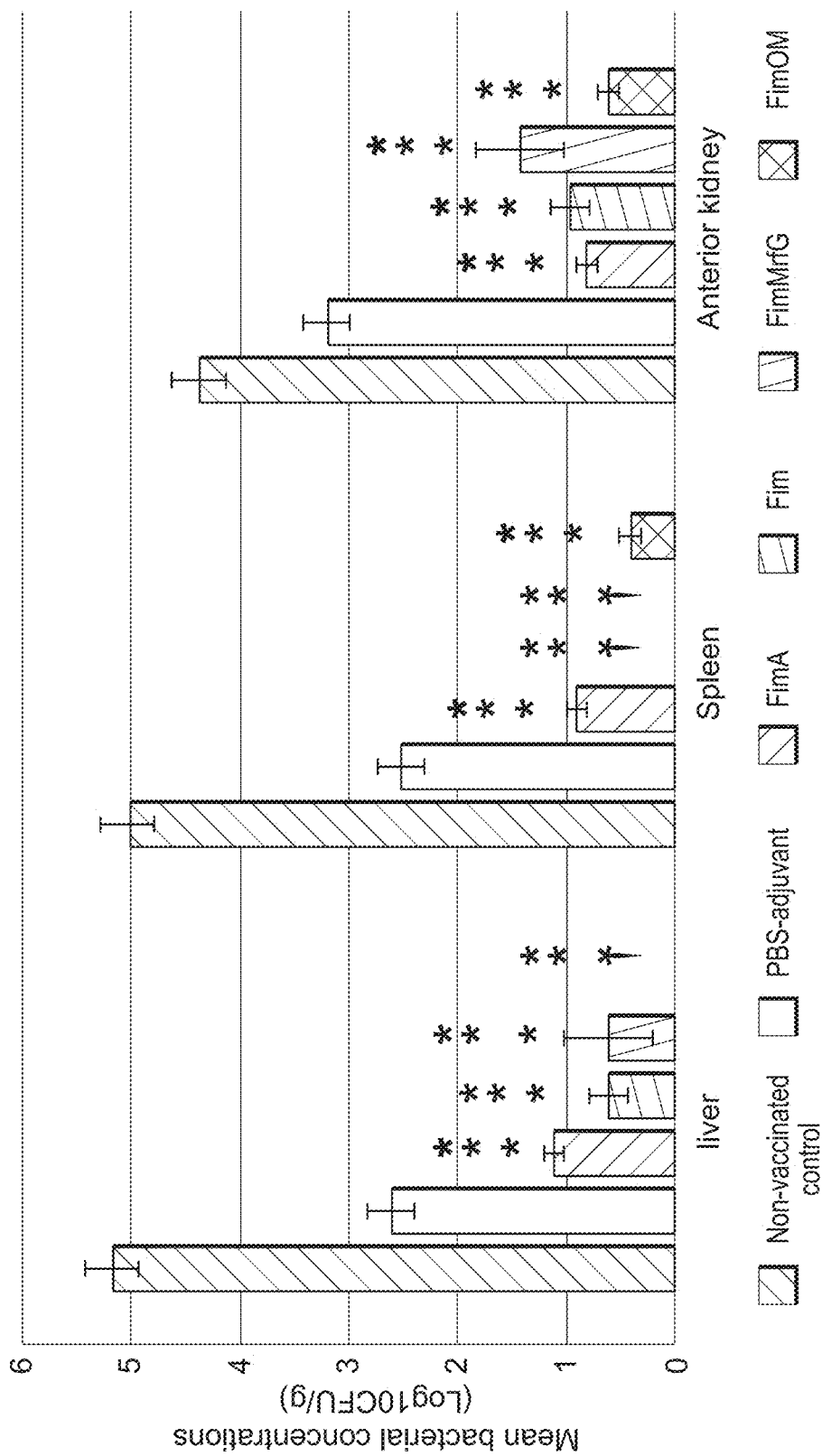
FIG. 4 is a bar graph showing mean bacterial concentrations (CFU/g) in liver (left), spleen (center), and anterior kidney (right) of catfish vaccinated with recombinant FimA, Fim, FimMrfG, and FimOM fimbrial proteins at 48 h post-infection with *A. hydrophila* ML09-119. Data represents the mean±SE of five fish per treatment. Significant differences between vaccinated and non-vaccinated treatments are indicated with asterisks (*) ($p<0.05$). Significant differences between vaccinated treatments and PBS-adjuvant treatment are indicated with two asterisks (‡) ($p<0.05$). † indicates CFU/g was below the detectable limit for this treatment.

Mean bacterial concentrations in liver were significantly lower (p<0.0003) in fish vaccinated with FimA, Fim, FimMrfG, and FimOM than both non-vaccinated fish and fish injected with PBS-adjuvant (FIG. 4). Furthermore, the mean spleen and anterior kidney bacterial loads were significantly lower (p<0.0001 and p<0.03, respectively) in fish vaccinated with the four recombinant fimbrial proteins compared to the non-vaccinated control treatment and the PBS-adjuvant treatment.

Serum Antibody Response

Figure 5:
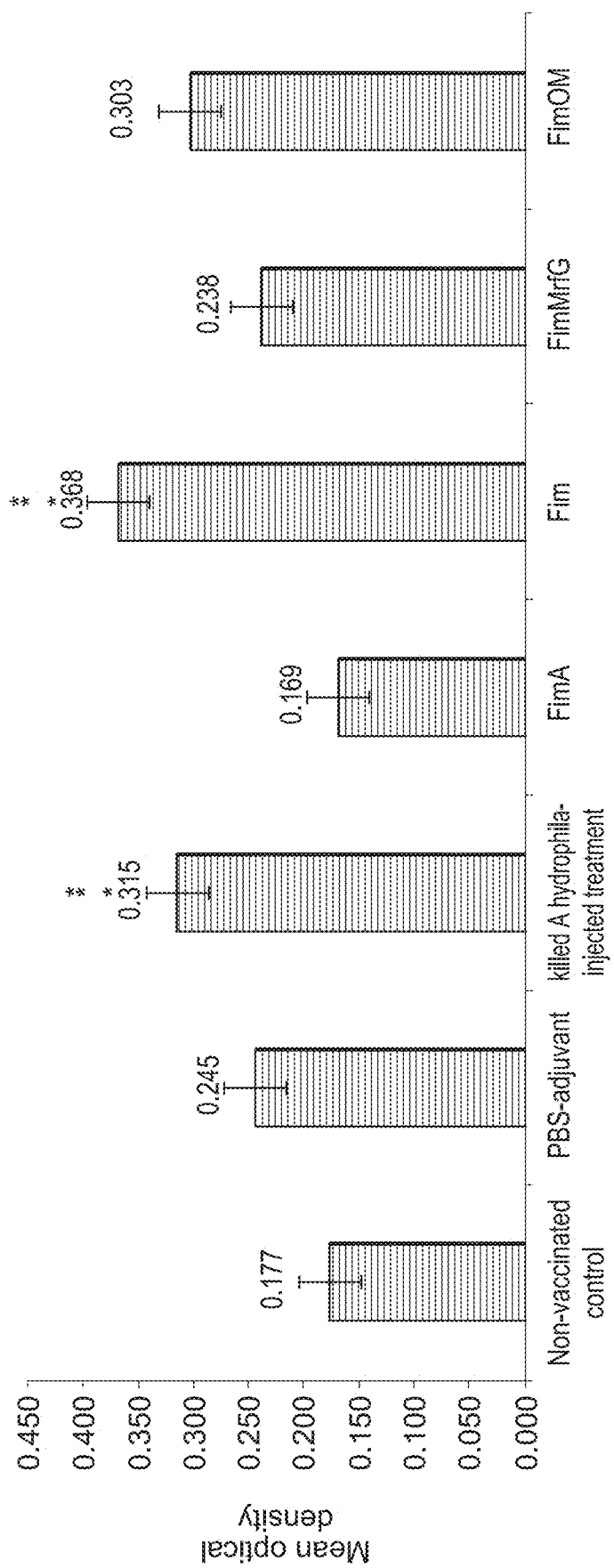
FIG. 5 is a bar graph showing antibody response determined by ELISA in channel catfish serum at 21 days post-vaccination with FimA, Fim, FimMrfG, and FimOM proteins. Optical densities at 405 nm are means of ten fish. Vertical bars denote standard errors of the mean. Asterisks (*) indicate statistically significant differences between non-vaccinated treatment and vaccinated treatments ($p<0.05$). Two asterisks (‡) indicate significant differences between vaccinated treatments and PBS adjuvant ($p<0.05$).

Fish vaccinated with Fim protein had significantly higher ($p=0.02$) antibody production than non-vaccinated fish and fish injected with PBS-adjuvant (FIG. 5). Fish injected with killed *A. hydrophila* also had significantly ($p<0.05$) higher antibody titers than non-vaccinated treatment. However, antibody response in fish vaccinated with FimA, FimMrfG, and FimOM did not significantly differ ($p=1.00$, 0.61, and 0.16, respectively) from non-vaccinated fish or the PBS-adjuvant treatment. Fish vaccinated with adjuvant only also did not have significantly higher antibody concentrations than non-vaccinated control treatment.

Discussion of Recombinant Fimbrial Protein Results

*A. hydrophila* strain ML09-119 represents a clonal group of *A. hydrophila* isolates causing outbreaks of bacterial septicemia in channel catfish since 2009. This isolate is significantly more virulent to channel catfish than historical *A. hydrophila* strains isolated from sporadic cases of MAS in fish and a Chinese carp isolate (Hossain et al., 2014). We compared the genome sequence of strain ML09-119 (GenBank accession no: CP005966.1) (Tekedar et al., 2013) with the *A. hydrophila* ATCC 7966T genome sequence (NC_008570.1) to identify four fimbrial proteins unique to ML09-119 (AGM42215.1, AGM42222.1, AGM42218.1, and AGM42220.1). We hypothesized that these proteins will be effective in stimulating significant protective immunity in catfish against strain ML09-119. Our aim was to identify protective protein antigens from virulent *A. hydrophila* for potential use as recombinant antigens that can be expressed in a live attenuated vaccine carrier or other appropriate vaccine formulation or carrier.

Fimbriae are adhesive organelles that are often important virulence factors in a wide range of pathogenic bacteria (Sauer et al., 2004). They typically facilitate invasion of host tissues and are involved in other diverse functions such as phage binding, DNA transfer, biofilm formation, cell aggregation, and twitching motility (Doughty et al., 2000; Kline et al., 2009; Proft and Baker, 2009). Fimbriae are divided into four classes based on their assembly pathways, of which the type I fimbriae are encoded by the fim gene cluster (Jones et al., 1995; Knight and Bouckaert, 2009). Type I fimbriae are the most prevalent type and are found on most uropathogenic *Escherichia coli* (UPEC), where they contribute significantly to urinary tract infection. Type 1 fimbriae are also responsible for invasion and persistence in target cells (Baorto et al., 1997). They are found in several species, including *Salmonella enterica, Pseudomonas putida, Klebsiella pneumoniae*, and *Yersinia* (Sauer et al., 2004).

Due to their extracellular location and their role in colonizing host tissue, fimbrial proteins have been considered important targets for vaccine development against several bacterial diseases. For instance, purified recombinant FimA induces protective immunity against *Edwardsiella tarda* in turbot fish, suggesting that rFimA is an effective subunit vaccine (Wang et al., 2013a). In *Proteus mirabilis*, a common cause of urinary tract infection, structural fimbrial protein (MrpA) protects mice from infection when used as a purified recombinant protein (Pellegrino et al., 2003). Immunization of pigs with the Type IV fimbrial recombinant protein of *Actinobacillus pleuropneumoniae* induces high levels of protection that could be a valuable component of an efficient subunit vaccine for the prevention of porcine pleuropneumonia (Sadilkova et al., 2012).

The pET plasmids are very effective for expression of recombinant proteins in *E. coli* based on the T7 promoter (Rosenberg et al., 1987), and we found it to be effective for expression of the four fimbrial *A. hydrophila* genes fimA, fim, fimMrfG, and fimOm encoding structural fimbrial subunits. The four recombinant proteins were found in the insoluble fraction during purification, which is consistent with what was observed for *P. mirabilis* fimbrial proteins (Sauer et al., 2004). It is possible that the expressed protein formed inclusion bodies due to overexpression.

The level of protection provided by the four proteins in catfish against experimental infection with *A. hydrophila* strain ML09-119 varied. Fish vaccinated with Fim and FimMrfG proteins had strong protection against *A. hydrophila* infection (RPS: 95.41% and 85.72%), while fish immunized with FimA and FimOM had less protection (RPS: 59.83% and 75.01%). The two most effective recombinant proteins as vaccines are structural fimbriae proteins.

Consistent with these findings, the mean bacterial counts recovered from liver, spleen, and anterior kidney of catfish vaccinated with FimA, Fim, FimMrfG, and FimOM were significantly lower than bacterial counts of non-vaccinated control group within 48 h post-infection. This indicates that all four proteins are effective at reducing infection caused by VAh, even though some are better at protecting the host fish than others. Mean bacterial concentrations from anterior kidney were more consistent and higher than spleen and liver, indicating that anterior kidney may be the preferred tissue for recovery and quantification of *A. hydrophila* during infection. However, posterior kidney was not tested in this study.

The antibody titers in non-vaccinated catfish serum may be due to environmental exposure to *A. hydrophila*, which is ubiquitous in aquatic environments (Janda and Abbott, 2010). Another factor likely contributing to the background antibody concentrations detected in non-vaccinated fish is that our plates were coated with whole cell lysate of *A. hydrophila* ML09-119. An alternative method that would yield more specific detection of antibody is to use respective recombinant proteins to coat ELISA plates.

In the current study, only Fim immunized catfish had a statistically significant increase in antibody concentration compared to the control non-vaccinated group. Fim vaccinated catfish also had the best protection against subsequent challenge with strain ML09-119, suggesting that humoral immunity contributes to protection against VAh infection. However, antibodies do not account for all of the protection, because fish vaccinated with FimA, FimMrfG, and FimOM all had significant protection but no significant increase in antibody concentration.

For some pathogens, anti-fimbrial antibodies show significant contributions to protection against infection. For example, vaccination of turbot fish with recombinant FimA as a subunit vaccine induced production of specific serum antibodies that bound live *E. tarda* via interaction with FimA. This antibody-*E. tarda* interaction effectively blocked infection (Wang et al., 2013a). Fimbrial protein of *Pasteurella multocida* is also antigenic and stimulated antibody production (IgG and IgA) in goats that provided good protection against high dose challenge (Ina Salwany, 2009; Mohd Yasin et al., 2011). In contrast, *Salmonella* fimbrial vaccines did not induce high antibody titers in poultry; however, they were very effective for control of experimental infection (Menão et al., 2013).

In conclusion, our results confirm our hypothesis that Fim can be used as a vaccine, as at least one component, against VAh infection in channel catfish. FimMrfG also provided good protection. Both of these proteins have potential for integration into a live attenuated vaccine carrier or maybe included in another appropriate vaccine formulation or vaccine carrier. The exact mechanism of this protective effect remains unknown, and future studies are needed to completely characterize the immune responses elicited by these A. hydrophila fimbrial proteins.

Results of Recombinant OMP Tests

Expression and Purification of Recombinant OmpAI, TonB-DR, and TbpA Proteins

The ompAI, tonB-DR, and tbpA genes of *A. hydrophila* strain ML09-119 were successfully cloned into pET-28a vector, and these constructs were confirmed by restriction enzyme analysis and DNA sequencing.

Figure 6:
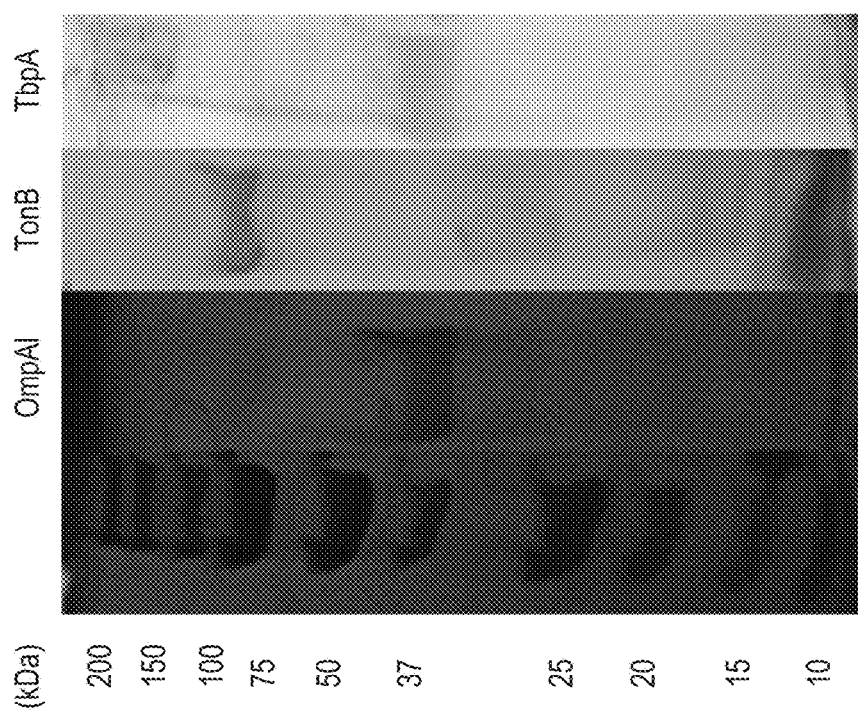
FIG. 6 depicts an SDS-PAGE gel stained with Coomassie blue stain showing purified recombinant OmpAI, TonB-dependent receptor, and TbpA proteins.

The induced recombinant cells started expression of OmpAI, TonB, and TbpA proteins at 2 h and reached a maximum level at 6 h. Thus, the optimal time for the expression was 6 h after IPTG induction. The expressed recombinant protein encoded for OmpAI, TonB-DR, and TbpA proteins were estimated to have molecular weights of 37.26, 78.55, and 41.67 kDa, respectively. The purified recombinant proteins showed single thick bands on SDS-PAGE (FIG. 6).

Vaccine Protective Efficacy of Recombinant OmpAI, TonB-DR, and TbpA Proteins

Figure 7:
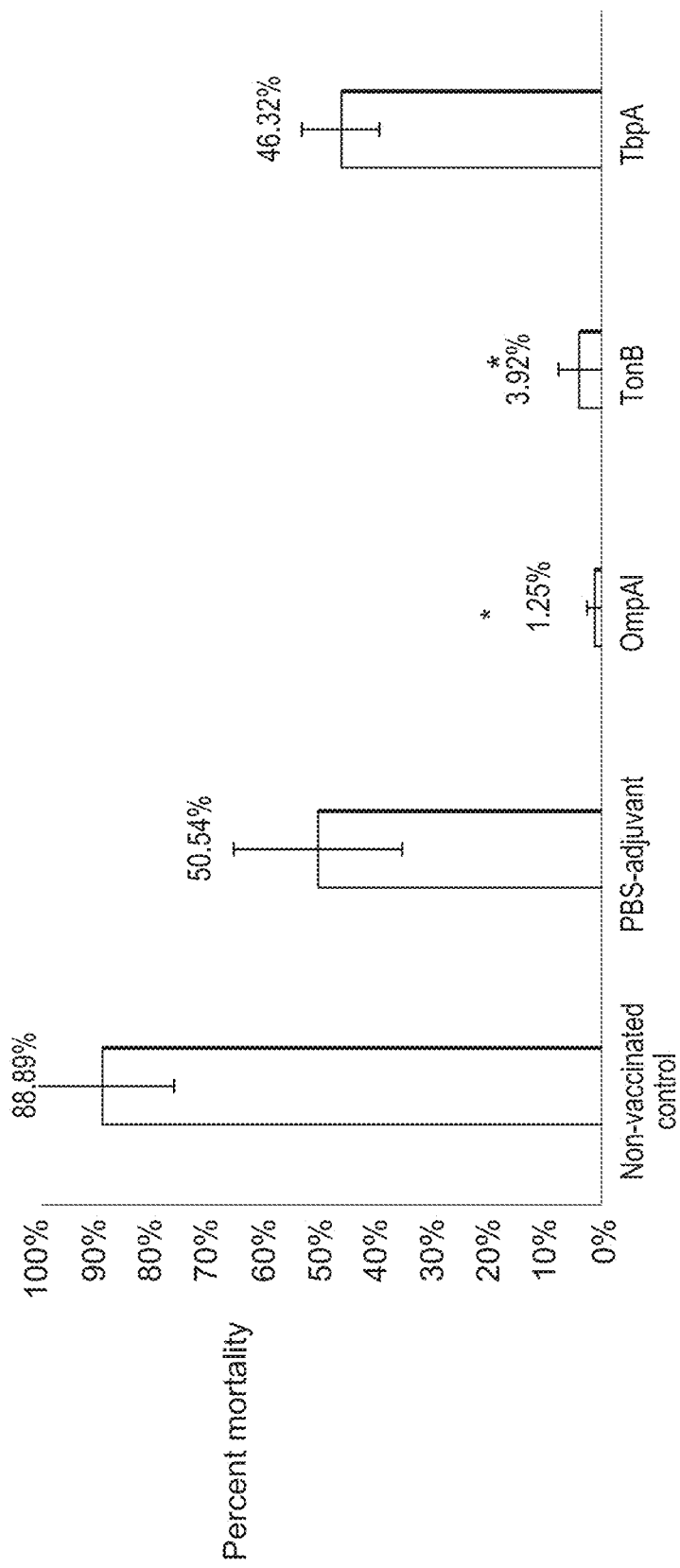
FIG. 7 is a bar graph showing percent mortalities in catfish challenged with *A. hydrophila* ML09-119 at 21 day post-vaccination with recombinant OmpAI, TonB-dependent receptor, and TbpA proteins. Significant differences between vaccinated and non-vaccinated treatments are indicated with asterisks (*) ($p<0.05$).

Significantly higher mortalities occurred in the non-vaccinated group (88.89%) compared with fish vaccinated with OmpAI (1.25%; p=0.0021) and TonB-DR (3.92%; p=0.0051) after challenge with *A. hydrophila* strain ML09-119. Fish immunized with TbpA had less mortality (46.32%) than both the non-vaccinated treatment and fish injected with PBS-adjuvant (50.54%); however these differences were not significant (p=0.065 and 0.899, respectively). In terms of the RPS for the fish vaccinated with OmpA1, TonB-DR, TbpA, and PBS-adjuvant were 98.59%, 95.59%, 47.89%, and 43.14%, respectively (FIG. 7).

Figure 8:
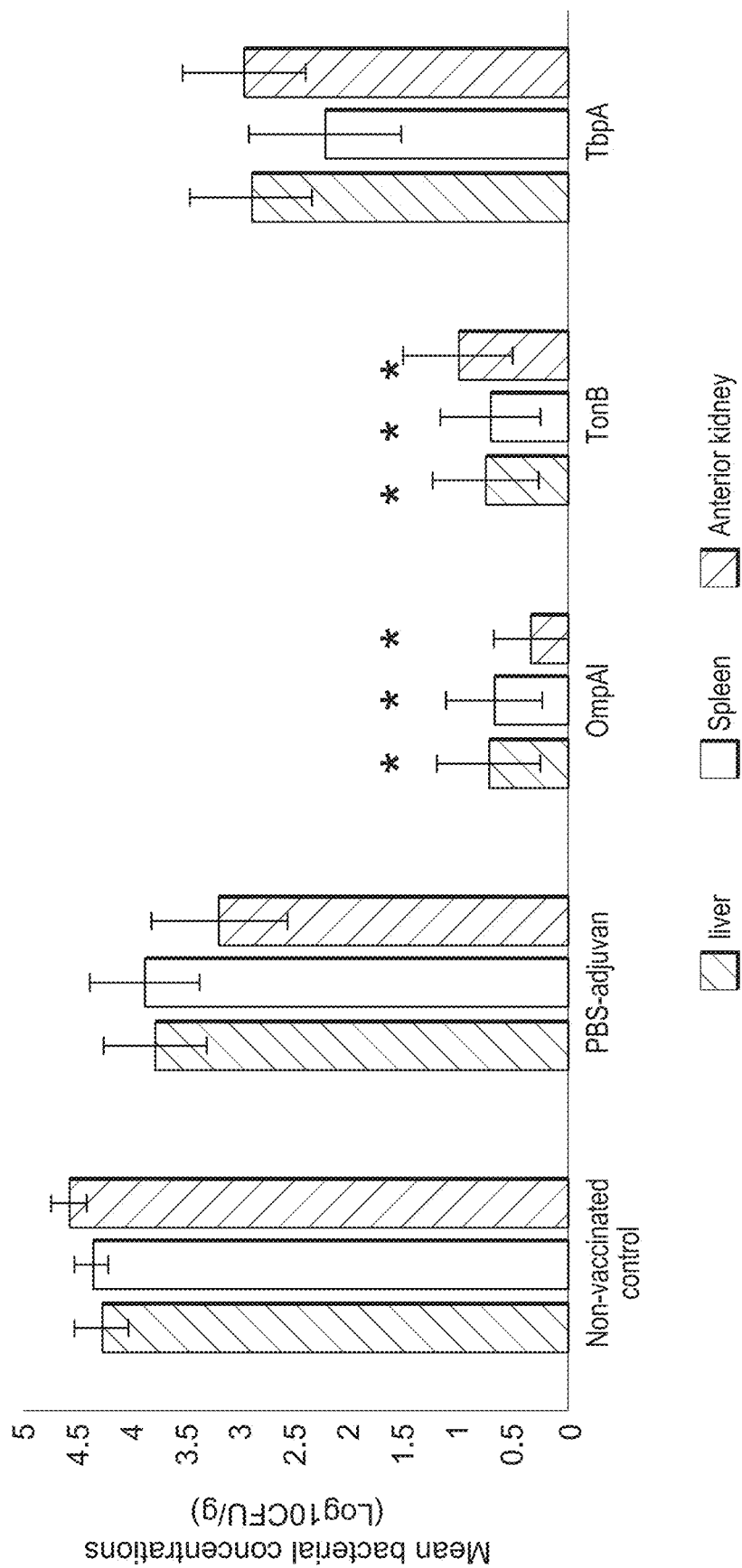
FIG. 8 is a bar graph showing mean bacterial concentrations (CFU/g) in liver, spleen, and anterior kidney of catfish vaccinated with recombinant OmpAI, TonB-dependent receptor, and TbpA proteins at 48 h post-infection with *A. hydrophila* ML09-119. Data are presented as means±SE. Significant differences between vaccinated and non-vaccinated treatments are indicated with asterisks (*) ($p<0.05$).

*Aeromonas hydrophila* counts in liver, spleen, and anterior kidney were significantly lower in fish vaccinated with OmpAI and TonB-DR compared with non-vaccinated fish (p<0.005). However, mean bacterial counts in tissues from fish vaccinated with TbpA were subjectively lower than the control group, but did not differ significantly (p>0.005) (FIG. 8).

Fish Serum Antibody Response of Recombinant OmpAI, TonB-DR, and TbpA Proteins

Figure 9:
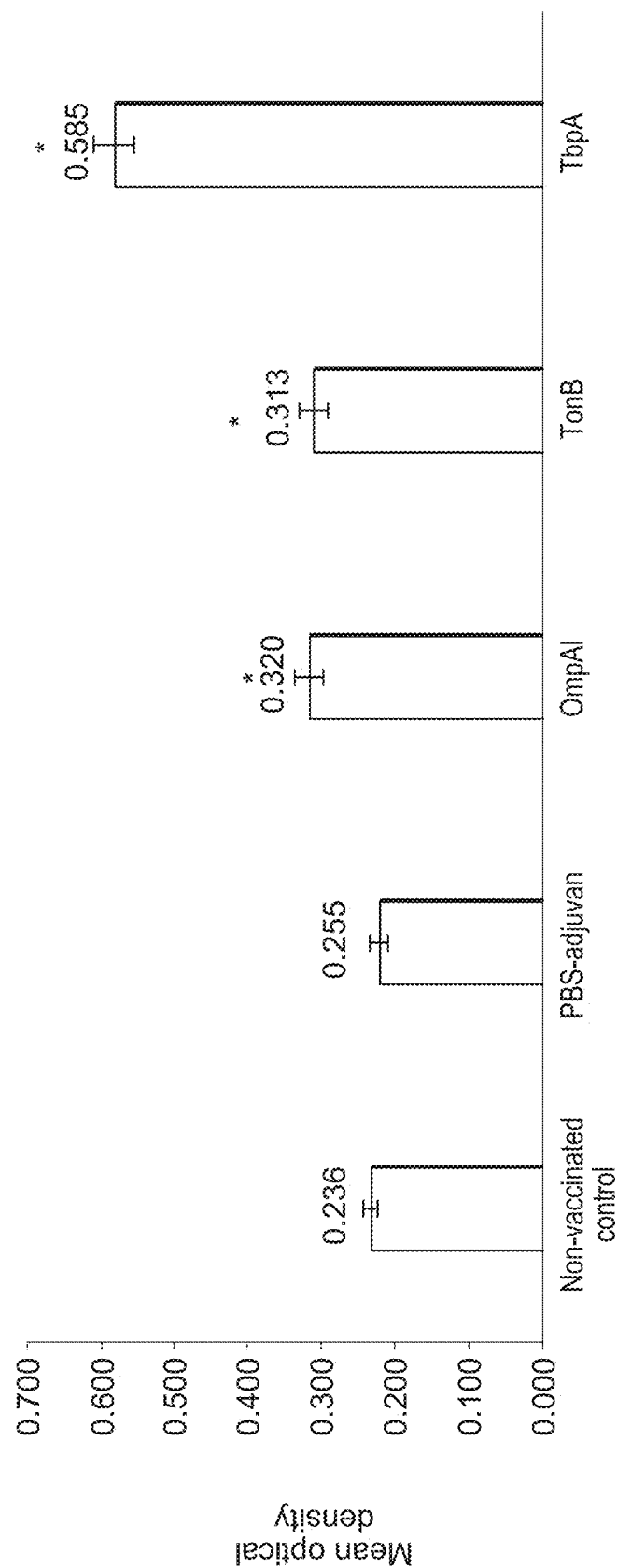
FIG. 9 is a bar graph showing antibody response determined by ELISA in channel catfish serum at day 21 post-vaccination with OmpAI, TonB-dependent receptor, and TbpA proteins. The data represent the mean of optical densities at 405 nm of 8 fish. Vertical bars denote standard errors of the mean. Asterisks (*) indicate statistically significant differences between vaccinated and non-vaccinated fish ($p<0.05$).

Catfish immunized with the OmpAI, TonB-DR, and TbpA proteins had significantly higher antibody titers (as expressed as an optical density of 450 nm) than both the non-vaccinated group (p=0.0040, 0.0065, and 0.001, respectively), and PBS-adjuvant treatment (p=0.0001, 0.0003, and 0.001, respectively). Higher antibody responses were detected in fish vaccinated with TbpA than fish vaccinated with either OmpAI or TonB-DR proteins (FIG. 9).

Discussion of Recombinant OMP Results

Several OMPs are being studied as potential candidates for vaccine development for several bacterial infections (Kawai et al., 2004; Sakai et al., 2009). Because of their location (they comprise the outermost surface in contact with host cells), OMPs are immunologically important structures that have protective antigenicity. OMPs are also known to be associated with pathogenesis and play a key role during the initial processes of bacterial adhesion and invasion. Purified OMPs of *A. hydrophila* have been shown to be immunogenic in fish, such as the blue gourami, goldfish, European eel, and Indian major carp (Fang H M, 2000; Guan et al., 2011; Khushiramani et al., 2007; Rahman and Kawai, 2000).

Genomic subtraction identified three OMPs (OmpAI, TonB-DR, and TbpA) that are present in the epidemic isolates and absent from avirulent strains of *A. hydrophila*. These three proteins seem to be directly related to the virulence of *A. hydrophila* ML09-119 strain. In this study, we purified OmpAI, TonB-DR, and TbpA proteins of *A. hydrophila* strain ML09-119, and we evaluated the protection efficacy of those proteins against *A. hydrophila* epidemic strain infection in catfish.

Results from the bacterial challenge experiment show that fish vaccinated with OmpAI and TonB-DR proteins were well protected when challenged with virulent *A. hydrophila* relative to the non-vaccinated fish and resulted in a high RPS (98.59% and 95.59%, respectively). Fish vaccinated with TbpA showed moderate protection with 47.89% RPS. The fish injected with PBS-adjuvant had less mortality compared with non-vaccinated fish which indicated that the adjuvant had a possible effect on protection. However, most commercial injectable vaccines contain oil-adjuvants (Sommerset et al., 2005). Consistent with protection response, the *A. hydrophila* counts recovered from liver, spleen, and anterior kidney of catfish vaccinated with OmpAI and TonB-DR were significantly lower than bacterial counts of the non-vaccinated fish within 48 h post-infection. Conversely, bacterial counts from fish injected with TbpA were not significantly lower than controls.

Previous studies by other researchers demonstrated that OmpA and TonB-dependent receptor proteins could be used as immunogens to protect non-catfish species of fish against infection from some bacteria strains. For example, common carp vaccinated with recombinant OmpA purified from *Edwardsiella tarda* showed a higher survival rate (60%) as compared to un-immunized fish against *E. tarda* infection (Maiti et al., 2011). In another study, the recombinant Omp48 of *A. hydrophila* showed significant protection in fish against both *A. hydrophila* and *E. tarda* infections (RPS: 69 and 60%, respectively) and could be used as a potential vaccine candidate (Khushiramani et al., 2012). Later, Chinese breams vaccinated with recombinant Omp38 of *A. hydrophila* were well protected when challenged with virulent *A. hydrophila* with 57.14 RPS of vaccinated fish was (Wang et al., 2013b). Japanese flounder vaccinated with TonB-dependent receptors had 80.6% RPS against *Pseudomonas fluorescens* infection (Hu et al., 2012), and a study with *N. meningitidis* showed that TonB-dependent receptors could induce bactericidal antibodies upon immunization of mice (Stork et al., 2010). The differences in RPS between our results and these studies may be due to fish species, the time elapsed between vaccination and challenge, bacterial dose, inoculation method, and adjuvant effect.

In the current study, the antibody responses of the fish vaccinated with OmpAI, TonB-DR, and TbpA were measured by ELISA at 21 days post-immunization. Our data demonstrated that the antibody response after immunization with OmpAI and TonB-DR proteins did not correlate with the protection level. This may reflect a predominance of the cellular immune reactions over the humoral response in fish (Hernanz Moral et al., 1998; Marsden et al., 1996). Different studies have been unable to establish a clear correlation between a humoral response and protection against *A. hydrophila* (Baba et al., 1988; Stevenson, 1988).

In the present study, fish vaccinated with TbpA failed to provide strong protection, however TbpA injection provided a high antibody response. Although TbpA and TbpB proteins have generated particular interest as vaccine antigens, either alone or in combination, some questions have been raised about the protection efficacy and immune response of TbpA (Martinez et al., 2010). In contrast to OmpAI and TonB-DR, there is no clear evidence that TbpA could serve as an effective vaccine antigen through the production of functional antibody. Some studies have provided results indicating that immunization with recombinant TbpA protein from the *Pasteurella haemolytica* (Potter et al., 1999), *H. influenzae* (Loosmore et al., 1996), *M. catarrhalis* (Myers et al., 1998) or native TbpA from *N. meningitidis* (Lissolo et al., 1995) provided an antibody response that did not demonstrate bactericidal activity or protection in passive immunotherapy. Indeed, the recombinant TbpA fragment from *H. parasuis* (38.5 kDa, corresponding to 200 amino acids) showed very weak protection (Frandoloso et al., 2011; O'Neill et al., 1998). In agreement with these studies, our data confirmed that catfish immunized with TbpA produce a high antibody titer without strong protection against *A. hydrophila*. It has been postulated that the failure to produce functional antibody was due to the lack of native conformation in the TbpA preparations (Ala'Aldeen et al., 1994). However, in other studies it has been observed that TbpA from *Actinobacillus pleuropneumonias* (Kim and Lee, 2006) can induce protection and might be useful as an antigen for a vaccine.

The OmpA protein is among the most immunodominant antigens in the OM (Singh et al., 2003). In a previous study, a rOmpA protein elicited high antibody production in both common carp and rabbit against *E. tarda* infection (Maiti et al., 2011). In another study, high antibody titer developed in rainbow trout immunized with OmpA purified from *Flavobacterium psychrophilum* and emulsified with Freund's adjuvant (Dumetz et al., 2007). Previously, OMPs of *E. tarda* could elicit strong and persistent immune responses in Japanese flounder at 28 and 49 day-post injection, and then declined gradually (Tang et al., 2010). However, some studies have suggested that antibodies specific for OmpA or homologs did not confer passive protection (Gatto et al., 2002; Vasfi Marandi and Mittal, 1997). In a previous study, purified recombinant TonB dependent outer membrane receptor was able to induce strong protective immunity as a subunit vaccine used to immunize Japanese flounder (Hu et al., 2012).

In conclusion, vaccination of catfish with OmpA and TonB-dependent receptor provide high protection and stimulated moderate antibody responses, whereas TbpA provides less protection with a high antibody response. Results clearly indicate that the recombinant OmpAI and TonB proteins of *A. hydrophila* ML09-119 would contribute to an effective vaccine against *A. hydrophila* infection in catfish in a live-attenuated vaccine carrier or another appropriate vaccine formulation or vaccine carrier.

ATPase as a Vaccination Antigen for *A. hydrophila*

The ATPase protein (ATPase locus tag: AHML_21010) was also found to induce immune response and provide protection in catfish fingerlings against *A. hydrophila* ML09-119 infection. The ATPase protein of *A. hydrophila* ML09-119 has a molecular weight of 81.5100 kDa. The genomic DNA of ATPase was amplified from *A. hydrophila* ML09-119 and cloned into expression vector pET-28a (following the methods as described above). The recombinant clones encoding ATPase were successfully purified from *E. coli* on large scale and confirmed by SDS-PAGE analysis (following the methods as described above). The recombinant ATPase was then mixed with the non-mineral oil adjuvant Montanide ISA 763 AVG at a ratio of 30:70. An assay was conducted using recombinant OmpA1, TonB-DR, ATPase, and FimMrfG. When catfish fingerlings were vaccinated by intraperitoneal injection with the OmpA1, TonB-DR, ATPase, and FimMrfG, 98.75%, 96.08%, 89.16%, and 85.72% of the fish were protected against subsequent *A. hydrophila* ML09-119 infection. Furthermore, the mean liver, spleen, and anterior kidney bacterial loads were significantly lower in catfish vaccinated with the OmpA1, TonB-DR, ATPase, and FimMrfG than the non-vaccinated control group.

Live Attenuated Vaccine Combination

We developed a strategy to combine the advantages of a live attenuated vaccine (ESC-NDKL1 ($\Delta$gcvP$\Delta$sdhC$\Delta$frdA) mutant of *Edwardsiella ictaluri*—see U.S. Pat. No. 9,375,467 and U.S. application Ser. No. 15/171,367 for live attenuated vaccines against *Edwardsiella ictaluri*, both of which are incorporated herein by reference in their entirety to the extent not inconsistent with the present disclosure) against enteric septicemia of catfish (ESC) and three immunogenic recombinant proteins (Fim, FimMrfg, and ATPase) against *A. hydrophila* infection. We used ESC-NDKL1 vaccine candidate strain as a delivery vehicle for three recombinant plasmids (pETfim, pETmrfG, pETatpase). The recombinant plasmids were conjugated from *E. coli* to the ESC-NDKL1 strain. The virulence of the ESC-NDKL1 strains, harboring an expression vector with each of the recombinant proteins, were evaluated in vivo in catfish fingerlings. In a first study, our results showed channel catfish fingerlings immersion-vaccinated with ESC-NDKL1::pETfim, ESC-NDKL1::pETmrfG, and ESC-NDKL1::pETATPase exhibited 100%, 91.67%, and 100% percent survival after challenge with the *A. hydrophila* ML09-119, which was significantly less than non-vaccinated group (88.89% mortality).

Figure 10:
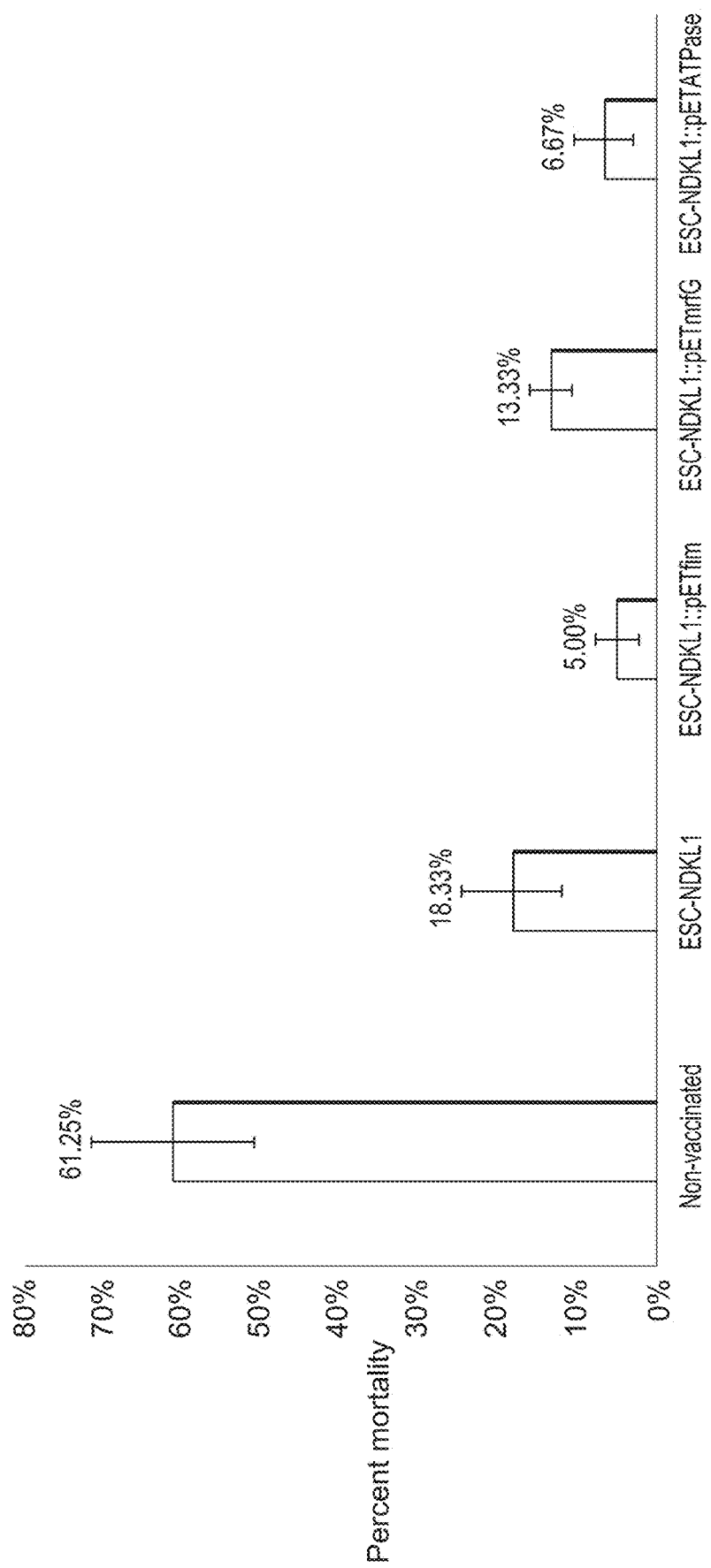
FIG. 10 is a bar graph showing percent mortalities in catfish fingerlings vaccinated with ESC-NDKL1::pETfim, ESC-NDKL1::pETmrfG, and ESC-NDKL1::pETATPase after experimental infection with *A. hydrophila* strain ML09-119 at 21 days post-immunization.

For vaccination in a second study, channel catfish fingerlings were divided into five groups: ESC-NDKL1::pETfim, ESC-NDKL1::pETmrfG, ESC-NDKL1::pETATPase, ESC-NDKL1, and sham-vaccinated. Catfish were vaccinated by immersion exposure with $10^7$ CFU/ml of recombinant ESC-NDKL1 for 1 h. At 21 days post-vaccination, all fish were challenged with *A. hydrophila* ML09-119 (approximately $10^{10}$ CFU/ml), and mean percent mortalities per tank were compared. Catfish immunized with NDKL1::pETfim, ESC-NDKL1::pETmrfG, ESC-NDKL1::pETATPase had significantly ($p<0.05$) lower mortalities than sham-vaccinated group (FIG. 10). Surprisingly, ESC-NDKL1 also provided significant protection against a challenge of *A. hydrophila* ML09-119, but, on average, the combination live attenuated vaccines outperformed the ESC-NDKL1 vehicle control. In summary, our data shows that recombinant proteins Fim, FimMrfG, OmpAI, TonB, and ATPase have potential as vaccine antigens against VAh infection, and ESC-NDKL1 is a potentially effective delivery vehicle for VAh antigens. Furthermore, other live attenuated vaccine carriers for *E. ictaluri* or other bacteria, as well as other vaccine formulation carriers, could be used to create single or combination vaccine strategies against VAh.

REFERENCES

Ala'Aldeen, D. A., Stevenson, P., Griffiths, E., Gorringe, A. R., Irons, L. I., Robinson, A., Hyde, S., Borriello, S. P., 1994. Immune responses in humans and animals to meningococcal transferrin-binding proteins: implications for vaccine design. Infection and immunity 62, 2984-2990.

Alvarez, B., Alvarez, J., Menendez, A., Guijarro, J. A., 2008. A mutant in one of two exbD loci of a TonB system in *Flavobacterium psychrophilum* shows attenuated virulence and confers protection against cold water disease. Microbiology 154, 1144-1151.

Amend, D. F., 1981. Potency testing of fish vaccines. Developments in Biological Standardization Vol. 49, 447-454.

Baba, T., Imamura, J., Izawa, K., Ikeda, K., 1988. Immune protection in carp, *Cyprinus carpio L., after immunization with Aeromonas hydrophila* crude lipopolysaccharide. Journal of Fish Diseases 11, 237-244.

Baorto, D. M., Gao, Z., Malaviya, R., Dustin, M. L., van der Merwe, A., Lublin, D. M., Abraham, S. N., 1997. Survival of FimH-expressing enterobacteria in macrophages relies on glycolipid traffic. Nature 389, 636-639.

Cornelissen, C. N., Biswas, G. D., Tsai, J., Paruchuri, D. K., Thompson, S. A., Sparling, P. F., 1992. Gonococcal transferrin-binding protein 1 is required for transferrin utilization and is homologous to TonB-dependent outer membrane receptors. Journal of bacteriology 174, 5788-5797.

Cornelissen, C. N., Sparling, P. F., 1994. Iron piracy: acquisition of transferrin-bound iron by bacterial pathogens. Molecular microbiology 14, 843-850.

Doughty, S. W., Ruffolo, C. G., Adler, B., 2000. The type 4 fimbrial subunit gene of *Pasteurella multocida*. Veterinary microbiology 72, 79-90.

Dumetz, F., Lapatra, S. E., Duchaud, E., Claverol, S., Le Henaff, M., 2007. The *Flavobacterium psychrophilum* OmpA, an outer membrane glycoprotein, induces a humoral response in rainbow trout. Journal of applied microbiology 103, 1461-1470.

Ebanks, R. O., Goguen, M., McKinnon, S., Pinto, D. M., Ross, N. W., 2005. Identification of the major outer membrane proteins of *Aeromonas salmonicida*. Diseases of aquatic organisms 68, 29-38.

Esteve, C., Amaro, C., Garay, E., Santos, Y., Toranzo, A. E., 1995. Pathogenicity of live bacteria and extracellular products of motile *Aeromonas* isolated from eels. Journal of Applied Bacteriology 78, 555-562.

Fang H M, L. K. C., Ge R and Sin M., 2000. Enhancement of protective immunity in blue gourami, Trichogaster trichopterus (Pallas), against *Aeromonas hydrophila* and *Vibrio anguillarum* by *A. hydrophila* major adhesion. Journal of Fish Diseases 23, 137"145.

Fang, H. M., Ge, R., Sin, Y. M., 2004. Cloning, characterisation and expression of *Aeromonas hydrophila* major adhesin. Fish & shellfish immunology 16, 645-658.

Frandoloso, R., Martinez, S., Rodriguez-Ferri, E. F., Garcia-Iglesias, M. J., Perez-Martinez, C., Martinez-Fernandez, B., Gutierrez-Martin, C. B., 2011. Development and characterization of protective *Haemophilus parasuis* subunit vaccines based on native proteins with affinity to porcine transferrin and comparison with other subunit and commercial vaccines. Clinical and vaccine immunology: CVI 18, 50-58.

Gatto, N. T., Dabo, S. M., Hancock, R. E., Confer, A. W., 2002. Characterization of, and immune responses of mice to, the purified OmpA-equivalent outer membrane protein of *Pasteurella multocida* serotype A:3 (Omp28). Veterinary microbiology 87, 221-235.

Gray-Owen, S. D., Loosmore, S., Schryvers, A. B., 1995. Identification and characterization of genes encoding the human transferrin-binding proteins from *Haemophilus influenzae*. Infection and immunity 63, 1201-1210.

Gresham, J., 2014. Producers, researchers will ramp up *Aeromonas* efforts in 2015. Catfish J. 27, 10.

Griffin, M. J., Goodwin, A. E., Merry, G. E., Liles, M. R., Williams, M. A., Ware, C., Waldbieser, G. C., 2013. Rapid quantitative detection of *Aeromonas hydrophila* strains associated with disease outbreaks in catfish aquaculture. Journal of veterinary diagnostic investigation: official publication of the American Association of Veterinary Laboratory Diagnosticians, Inc 25, 473-481.

Guan, R., Xiong, J., Huang, W., Guo, S., 2011. Enhancement of protective immunity in European eel (Anguilla anguilla) against *Aeromonas hydrophila* and *Aeromonas sobria* by a recombinant *Aeromonas* outer membrane protein. Acta biochimica et biophysica Sinica 43, 79-88.

Hemstreet, B., 2010. An update on *Aeromonas hydrophila* from a fish health specialist for summer 2010. Catfish Journal 24.

Hernanz Moral, C., Flano del Castillo, E., Lopez Fierro, P., Villena Cortes, A., Anguita Castillo, J., Cascon Soriano, A., Sanchez Salazar, M., Razquin Peralta, B., Naharro Carrasco, G., 1998. Molecular characterization of the *Aeromonas hydrophila* aroA gene and potential use of an auxotrophic aroA mutant as a live attenuated vaccine. Infection and immunity 66, 1813-1821.

Hossain, M. J., Waldbieser, G. C., Sun, D., Capps, N. K., Hemstreet, W. B., Carlisle, K., Griffin, M. J., Khoo, L., Goodwin, A. E., Sonstegard, T. S., Schroeder, S., Hayden, K., Newton, J. C., Terhune, J. S., Liles, M. R., 2013. Implication of lateral genetic transfer in the emergence of *Aeromonas hydrophila* isolates of epidemic outbreaks in channel catfish. PloS one 8, e80943.

Hossain, M. J., Sun, D., McGarey, D. J., Wrenn, S., Alexander, L. M., Martino, M. E., Xing, Y., Terhune, J. S., Liles, M. R., 2014. An Asian origin of virulent *Aeromonas hydrophila* responsible for disease epidemics in United States-farmed catfish. mBio 5, e00848-00814.

Hu, Y. H., Dang, W., Sun, L., 2012. A TonB-dependent outer membrane receptor of *Pseudomonas fluorescens*: virulence and vaccine potential. Archives of microbiology 194, 795-802.

Ina Salwany, M. Y., 2009. Identification, cloning, sequencing, expression and protective capacity of the gene encoding a fimbrial protein of *Pasteurella multocida* B:2. Faculty of Science and Technology, University Malaysia Terengganu.

Irwin, S. W., Averil, N., Cheng, C. Y., Schryvers, A. B., 1993. Preparation and analysis of isogenic mutants in the transferrin receptor protein genes, tbpA and tbpB, from *Neisseria meningitidis*. Molecular microbiology 8, 1125-1133.

Janda, J. M., Abbott, S. L., 2010. The genus *Aeromonas*: taxonomy, pathogenicity, and infection. Clinical microbiology reviews 23, 35-73.

Jones, C. H., Pinkner, J. S., Roth, R., Heuser, J., Nicholes, A. V., Abraham, S. N., Hultgren, S. J., 1995. FimH adhesin of type 1 pili is assembled into a fibrillar tip structure in the Enterobacteriaceae. Proceedings of the National Academy of Sciences of the United States of America 92, 2081-2085.

Kawai, K., Liu, Y., Ohnishi, K., Oshima, S., 2004. A conserved 37 kDa outer membrane protein of *Edwardsiella tarda* is an effective vaccine candidate. Vaccine 22, 3411-3418.

Kenney, C. D., Cornelissen, C. N., 2002. Demonstration and characterization of a specific interaction between gonococcal transferrin binding protein A and TonB. Journal of bacteriology 184, 6138-6145.

Khushiramani, R., Girisha, S. K., Karunasagar, I., Karunasagar, I., 2007. Cloning and expression of an outer membrane protein ompTS of *Aeromonas hydrophila* and study of immunogenicity in fish. Protein Expression and Purification 51, 303-307.

Khushiramani, R. M., Maiti, B., Shekar, M., Girisha, S. K., Akash, N., Deepanjali, A., Karunasagar, I., Karunasagar, I., 2012. Recombinant *Aeromonas hydrophila* outer membrane protein 48 (Omp48) induces a protective immune response against *Aeromonas hydrophila* and *Edwardsiella tarda*. Research in microbiology 163, 286-291.

Kim, T., Lee, J., 2006. Cloning and expression of genes encoding transferrin-binding protein A and B from *Actinobacillus pleuropneumoniae* serotype 5. Protein Expr Purif 45, 235-240.

Kline, K. A., Fälker, S., Dahlberg, S., Normark, S., Henriques-Normark, B., 2009. Bacterial Adhesins in Host-Microbe Interactions. Cell Host & Microbe 5, 580-592.

Knight, S., Bouckaert, J. 2009. Structure, Function, and Assembly of Type 1 Fimbriae, In: Lindhorst, T. K., Oscarson, S. (Eds.) Glycoscience and Microbial Adhesion. Springer Berlin Heidelberg, 67-107.

Koebnik, R., Locher, K. P., Van Gelder, P., 2000. Structure and function of bacterial outer membrane proteins: barrels in a nutshell. Molecular microbiology 37, 239-253.

Laemmli, U. K., 1970. Cleavage of structural proteins during the assembly of the head of bacteriophage T4. Nature 227, 680-685.

Letain, T. E., Postle, K., 1997. TonB protein appears to transduce energy by shuttling between the cytoplasmic membrane and the outer membrane in *Escherichia coli*. Molecular microbiology 24, 271-283.

Lin, J., Huang, S., Zhang, Q., 2002. Outer membrane proteins: key players for bacterial adaptation in host niches. Microbes and infection/Institut Pasteur 4, 325-331.

Lissolo, L., Maitre-Wilmotte, G., Dumas, P., Mignon, M., Danve, B., Quentin-Millet, M. J., 1995. Evaluation of transferrin-binding protein 2 within the transferrin-binding protein complex as a potential antigen for future meningococcal vaccines. Infection and immunity 63, 884-890.

Lobb, C. J., Clem, L. W., 1982. Fish lymphocytes differ in the expression of surface immunoglobulin. Developmental and comparative immunology 6, 473-479.

Loosmore, S. M., Yang, Y. P., Coleman, D. C., Shortreed, J. M., England, D. M., Harkness, R. E., Chong, P. S., Klein, M. H., 1996. Cloning and expression of the *Haemophilus influenzae* transferrin receptor genes. Molecular microbiology 19, 575-586.

Luke, N. R., Campagnari, A. A., 1999. Construction and characterization of *Moraxella catarrhalis* mutants defective in expression of transferrin receptors. Infection and immunity 67, 5815-5819.

Mahasreshti, P. J., Murphy, G. L., Wyckoff, J. H., 3rd, Farmer, S., Hancock, R. E., Confer, A. W., 1997. Purification and partial characterization of the OmpA family of proteins of *Pasteurella haemolytica*. Infection and immunity 65, 211-218.

Maiti, B., Shetty, M., Shekar, M., Karunasagar, I., Karunasagar, I., 2011. Recombinant outer membrane protein A (OmpA) of *Edwardsiella tarda*, a potential vaccine candidate for fish, common carp. Microbiological Research 167, 1-7.

Maiti, B., Shetty, M., Shekar, M., Karunasagar, I., Karunasagar, I., 2012. Evaluation of two outer membrane proteins, Aha1 and OmpW of *Aeromonas hydrophila* as vaccine candidate for common carp. Veterinary immunology and immunopathology 149, 298-301.

Marsden, M. J., Vaughan, L. M., Foster, T. J., Secombes, C. J., 1996. A live (delta aroA) *Aeromonas salmonicida* vaccine for furunculosis preferentially stimulates T-cell responses relative to B-cell responses in rainbow trout (Oncorhynchus mykiss). Infection and immunity 64, 3863-3869.

Martinez, S., Frandoloso, R., Rodriguez-Ferri, E. F., Gonzalez-Zorn, B., Gutierrez-Martin, C. B., 2010. Characterization of a recombinant transferrin-binding protein A (TbpA) fragment from *Haemophilus parasuis* serovar 5. FEMS microbiology letters 307, 142-150.

Menão, M. C., Astolfi-Ferreira, C. S., Knöbl, T., Ferreira, A. J. P., 2013. Efficacy of bacterin-, outer membrane protein- and fimbriae extract-based vaccines for the control of *Salmonella Enteritidis* experimental infection in chickens. Pesquisa Veterinària Brasileira 33, 326-330.

Miller, N. W., Bly, J. E., van Ginkel, F., Ellsaesser, C. F., Clem, L. W., 1987. Phylogeny of lymphocyte heterogeneity: identification and separation of functionally distinct subpopulations of channel catfish lymphocytes with monoclonal antibodies. Developmental and comparative immunology 11, 739-747.

Mittal, R., Krishnan, S., Gonzalez-Gomez, I., Prasadarao, N. V., 2011. Deciphering the roles of outer membrane protein A extracellular loops in the pathogenesis of *Escherichia coli* K1 meningitis. The Journal of biological chemistry 286, 2183-2193.

Mohd Yasin, I. S., Mohd Yusoff, S., Mohd, Z. S., Abd Wahid Mohd, E., 2011. Efficacy of an inactivated recombinant vaccine encoding a fimbrial protein of *Pasteurella multocida* B:2 against hemorrhagic septicemia in goats. Tropical animal health and production 43, 179-187.

Myers, L. E., Yang, Y. P., Du, R. P., Wang, Q., Harkness, R. E., Schryvers, A. B., Klein, M. H., Loosmore, S. M., 1998. The transferrin binding protein B of *Moraxella catarrhalis* elicits bactericidal antibodies and is a potential vaccine antigen. Infection and immunity 66, 4183-4192.

O'Neill, H., Mayhew, S. G., Butler, G., 1998. Cloning and analysis of the genes for a novel electron-transferring flavoprotein from Megasphaera elsdenii. Expression and characterization of the recombinant protein. The Journal of biological chemistry 273, 21015-21024.

Pellegrino, R., Galvalisi, U., Scavone, P., Sosa, V., Zunino, P., 2003. Evaluation of *Proteus mirabilis* structural fimbrial proteins as antigens against urinary tract infections, Vol 36, 103-110 pp.

Potter, A. A., Schryvers, A. B., Ogunnariwo, J. A., Hutchins, W. A., Lo, R. Y., Watts, T., 1999. Protective capacity of the *Pasteurella haemolytica* transferrin-binding proteins TbpA and TbpB in cattle. Microbial pathogenesis 27, 197-206.

Power, M. L., Ferrari, B. C., Littlefield-Wyer, J., Gordon, D. M., Slade, M. B., Veal, D. A., 2006. A naturally occurring novel allele of *Escherichia coli* outer membrane protein A reduces sensitivity to bacteriophage. Applied and environmental microbiology 72, 7930-7932.

Pridgeon, J. W., Klesius, P. H., 2011. Molecular identification and virulence of three *Aeromonas hydrophila* isolates cultured from infected channel catfish during a disease outbreak in west Alabama (USA) in 2009. Diseases of Aquatic Organisms 94, 249-253.

Pridgeon, J. W., Klesius, P. H., Song, L., Zhang, D., Kojima, K., Mobley, J. A., 2013. Identification, virulence, and mass spectrometry of toxic ECP fractions of West Alabama isolates of *Aeromonas hydrophila* obtained from a 2010 disease outbreak. Veterinary microbiology 164, 336-343.

Proft, T., Baker, E. N., 2009. Pili in Gram-negative and Gram-positive bacteria—structure, assembly and their role in disease. Cell. Mol. Life Sci. 66, 613-635.

Rahman, M. H., Kawai, K., 2000. Outer membrane proteins of *Aeromonas hydrophila* induce protective immunity in goldfish. Fish Shellfish Immunol 10, 379-382.

Rosenberg, A. H., Lade, B. N., *Chui*, D. S., Lin, S. W., Dunn, J. J., Studier, F. W., 1987. Vectors for selective expression of cloned DNAs by T7 RNA polymerase. Gene 56, 125-135.

Sadilkova, L., Nepereny, J., Vrzal, V., Sebo, P., Osicka, R., 2012. Type IV fimbrial subunit protein ApfA contributes to protection against porcine pleuropneumonia. Veterinary research 43, 2.

Sakai, T., Matsuyama, T., Nishioka, T., Nakayasu, C., Kamaishi, T., Yamaguchi, K., Iida, T., 2009. Identification of major antigenic proteins of *Edwardsiella tarda* recognized by Japanese flounder antibody. Journal of veterinary diagnostic investigation: official publication of the American Association of Veterinary Laboratory Diagnosticians, Inc 21, 504-509.

Sauer, F. G., Remaut, H., Hultgren, S. J., Waksman, G., 2004. Fiber assembly by the chaperone-usher pathway. Biochimica et Biophysica Acta (BBA)-Molecular Cell Research 1694, 259-267.

Schryvers, A. B., Morris, L. J., 1988. Identification and characterization of the transferrin receptor from *Neisseria meningitidis*. Molecular microbiology 2, 281-288.

Schweizer, M., Henning, U., 1977. Action of a major outer cell envelope membrane protein in conjugation of *Escherichia coli* K-12. Journal of bacteriology 129, 1651-1652.

Shariff, M., 1998. Impact of diseases on aquaculture in the Asia-Pacific region as exemplified by epizootic ulcerative syndrome (EUS). Journal of Applied Ichthyology 14, 139-144.

Singh, S. P., Williams, Y. U., Miller, S., Nikaido, H., 2003. The C-terminal domain of *Salmonella enterica* serovar *typhimurium* OmpA is an immunodominant antigen in mice but appears to be only partially exposed on the bacterial cell surface. Infection and immunity 71, 3937-3946.

Sommerset, I., Krossoy, B., Biering, E., Frost, P., 2005. Vaccines for fish in aquaculture. Expert review of vaccines 4, 89-101.

Stevenson, R. M. W., 1988. Vaccination against *Aeromonas hydrophila*.

Stork, M., Bos, M. P., Jongerius, I., de Kok, N., Schilders, I., Weynants, V. E., Poolman, J. T., Tommassen, J., 2010. An outer membrane receptor of *Neisseria meningitidis* involved in zinc acquisition with vaccine potential. PLoS pathogens 6, e1000969.

Tang, X., Zhan, W., Sheng, X., Chi, H., 2010. Immune response of Japanese flounder Paralichthys *olivaceus* to outer membrane protein of *Edwardsiella tarda*. Fish Shellfish Immunol 28, 333-343.

Tauseef, I., Harrison, O. B., Wooldridge, K. G., Feavers, I. M., Neal, K. R., Gray, S. J., Kriz, P., Turner, D. P., Ala'Aldeen, D. A., Maiden, M. C., Bayliss, C. D., 2011. Influence of the combination and phase variation status of the haemoglobin receptors HmbR and HpuAB on meningococcal virulence. Microbiology 157, 1446-1456.

Tekedar, H. C., Waldbieser, G. C., Karsi, A., Liles, M. R., Griffin, M. J., Vamenta, S., Sonstegard, T., Hossain, M., Schroeder, S. G., Khoo, L., Lawrence, M. L., 2013. Complete Genome Sequence of a Channel Catfish Epidemic Isolate, *Aeromonas hydrophila* Strain ML09-119. Genome announcements 1.

Vasfi Marandi, M., Mittal, K. R., 1997. Role of outer membrane protein H (OmpH)- and OmpA-specific monoclonal antibodies from hybridoma tumors in protection of mice against *Pasteurella multocida*. Infection and immunity 65, 4502-4508.

Vazquez-Juarez, R. C., Romero, M. J., Ascencio, F., 2004. Adhesive properties of a LamB-like outer-membrane protein and its contribution to *Aeromonas veronii* adhesion. Journal of applied microbiology 96, 700-708.

Wang, C., Hu, Y. H., Chi, H., Sun, L., 2013a. The major fimbrial subunit protein of *Edwardsiella tarda*: vaccine potential, adjuvant effect, and involvement in host infection. Fish & shellfish immunology 35, 858-865.

Wang, N., Yang, Z., Zang, M., Liu, Y., Lu, C., 2013b. Identification of Omp38 by immunoproteomic analysis and evaluation as a potential vaccine antigen against *Aeromonas hydrophila* in Chinese breams. Fish & shellfish immunology 34, 74-81.

Waterstrat, P. R., Ainsworth, A. J., Capley, G., 1991. In vitro responses of channel catfish, *Ictalurus punctatus*, neutrophils to *Edwardsiella ictaluri*. Developmental and comparative immunology 15, 53-63.

Wimley, W. C., 2003. The versatile beta-barrel membrane protein. Current opinion in structural biology 13, 404-411.

Wu, L., Jiang, Y. N., Tang, Q., Lin, H. X., Lu, C. P., Yao, H. C., 2012. Development of an *Aeromonas hydrophila* recombinant extracellular protease vaccine. Microbial pathogenesis 53, 183-188.

Yadav, S. K., Sahoo, P. K., Dixit, A., 2014. Characterization of immune response elicited by the recombinant outer membrane protein OmpF of *Aeromonas hydrophila*, a potential vaccine candidate in murine model. Molecular biology reports 41, 1837-1848.

Yeh, H. Y., Klesius, P. H., 2012. Construction, expression and characterization of 11 putative flagellar apparatus genes of *Aeromonas hydrophila* AL09-73. Journal of fish diseases 35, 853-860.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A composition providing immunological protection from a disease caused by a pathogenic bacterial strain of *Aeromonas hydrophila*, said composition comprising a live attenuated vaccine ESC-NDKL1 (ΔgcvPΔsdhCΔfrdA) mutant of *Edwardsiella ictaluri* used as a delivery vehicle for any combination of the three recombinant proteins Fim, FimMrfG, and ATPase of *Aeromonas hydrophila*.

2. A method of providing immunological protection to an animal from a disease caused by a pathogenic bacterial strain of *Aeromonas hydrophila* in the animal comprising providing to the animal an effective amount of a live attenuated vaccine ESC-NDKL1 (ΔgcvPΔsdhCΔfrdA) mutant of *Edwardsiella ictaluri* used as a delivery vehicle for any combination of the five recombinant proteins Fim, FimMrfG, OmpAI, TonB, and ATPase of *Aeromonas hydrophila*.

3. A composition comprising a live attenuated vaccine ESC-NDKL1 (ΔgcvPΔsdhCΔfrdA) mutant of *Edwardsiella ictaluri* and any combination of recombinant proteins Fim, FimMrfG, OmpAI, TonB, and ATPase of *Aeromonas hydrophila*.

4. The composition of claim 3, wherein said live attenuated vaccine ESC-NDKL1 (ΔgcvPΔsdhCΔfrdA) mutant of *Edwardsiella ictaluri* consists of gene disrupting mutations in genes coding for three proteins in the group selected from glycine cleavage system (gcvP), succinate dehydrogenase (sdhC), malate dehydrogenase (mdh), and fumarate reductase (frdA).

5. A composition for stimulating immunological protection from disease caused by *Aeromonas hydrophila* comprising a live attenuated vaccine ESC-NDKL1 (ΔgcvPΔsdhCΔfrdA) mutant of *Edwardsiella ictaluri* and any combination of recombinant proteins Fim, FimMrfG, OmpAI, TonB, and ATPase of *Aeromonas hydrophila*.

6. A composition for providing immunological protection from disease caused by *Aeromonas hydrophila*, said composition comprising a recombinant protein of *Aeromonas hydrophila* selected from the group consisting of Fim, FimMrfG, OmpAI, TonB, and ATPase, wherein a live attenuated vaccine ESC-NDKL1 (ΔgcvPΔsdhCΔfrdA) mutant of *Edwardsiella ictaluri* is used as a delivery vehicle for any combination of the three recombinant proteins.

7. The composition of claim 6, wherein said live attenuated vaccine ESC-NDKL1 (ΔgcvPΔsdhCΔfrdA) mutant of *Edwardsiella ictaluri* consists of gene disrupting mutations in genes coding for three proteins in the group selected from glycine cleavage system (gcvP), succinate dehydrogenase (sdhC), malate dehydrogenase (mdh), and fumarate reductase (frdA).

* * * * *